US009545518B2

(12) United States Patent
Panken et al.

(10) Patent No.: US 9,545,518 B2
(45) Date of Patent: Jan. 17, 2017

(54) POSTURE STATE CLASSIFICATION FOR A MEDICAL DEVICE

(75) Inventors: Eric J. Panken, Edina, MN (US); Dennis M. Skelton, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 2256 days.

(21) Appl. No.: 12/432,993

(22) Filed: Apr. 30, 2009

(65) Prior Publication Data

US 2010/0010583 A1 Jan. 14, 2010

Related U.S. Application Data

(60) Provisional application No. 61/080,049, filed on Jul. 11, 2008.

(51) Int. Cl.
*A61N 1/00* (2006.01)
*A61N 1/365* (2006.01)
(Continued)

(52) U.S. Cl.
CPC ......... *A61N 1/36542* (2013.01); *A61B 5/1116* (2013.01); *A61B 5/7264* (2013.01);
(Continued)

(58) Field of Classification Search
CPC .......................... A61N 1/36542; A61B 5/1116
See application file for complete search history.

(56) References Cited

U.S. PATENT DOCUMENTS

| 4,297,685 A | 10/1981 | Brainard, II |
| 4,365,633 A | 12/1982 | Loughman |

(Continued)

FOREIGN PATENT DOCUMENTS

| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.
(Continued)

*Primary Examiner* — Edward Moran
*Assistant Examiner* — Nadia A Mahmood
(74) *Attorney, Agent, or Firm* — Beth L. McMahon

(57) ABSTRACT

Techniques for posture classification of a patient in a coordinate system of a sensor. According to one aspect, a defined vector is obtained from a sensor disposed in a substantially fixed manner relative to the patient. The defined vector is described in a coordinate system of the sensor and without regard to an orientation in which the sensor is disposed in relation to the patient. A detected vector is obtained from the sensor that is described using the coordinate system of the sensor. The detected vector and the defined vector to are used to classify the posture state of the patient without regard to the orientation in which the sensor is disposed in relation to the patient. A response may be initiated by a medical device, which may include adjusting therapy delivery.

55 Claims, 23 Drawing Sheets

(51) Int. Cl.
*A61B 5/11* (2006.01)
*A61B 5/00* (2006.01)

(52) U.S. Cl.
CPC ............ *A61B 5/1118* (2013.01); *A61B 5/686* (2013.01); *A61B 2562/0219* (2013.01); *A61N 1/36535* (2013.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,879,352 B1 * | 4/2005 | Kim ............................. 348/807 |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |

(56) References Cited

U.S. PATENT DOCUMENTS

| | | |
|---|---|---|
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,826,981 B2 | 11/2010 | Goode et al. |
| 8,529,448 B2 | 9/2013 | McNair |
| 8,649,862 B2 | 2/2014 | Ludwig et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253043 A1 | 11/2006 | Zhang et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0284979 A1* | 12/2006 | Clarkson ................. 348/143 |
| 2006/0287686 A1 | 12/2006 | Cullen et al. |
| 2007/0015976 A1 | 1/2007 | Miesel et al. |
| 2007/0032748 A1* | 2/2007 | McNeil et al. .............. 600/595 |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1* | 5/2007 | Wang et al. ................ 345/419 |
| 2007/0118056 A1* | 5/2007 | Wang et al. ................ 600/595 |
| 2007/0123758 A1 | 5/2007 | Miesel et al. |
| 2007/0129622 A1 | 6/2007 | Bourget et al. |

(56) References Cited

U.S. PATENT DOCUMENTS

| | | |
|---|---|---|
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/1050026 | 6/2007 | Bourget |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1* | 8/2008 | Sanghera et al. ............... 607/28 |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0106210 A1 | 4/2010 | Hedberg et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1731097 A2 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

(56) References Cited

OTHER PUBLICATIONS

Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Pschophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems, "ICECS 2002, 9$^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-157, Jan. 2006.
Kassam, "2005 EDP Topic "MK4": Tremor Data-Logger for Parkinson's Disease Patients,"http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare 10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-McKinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9$^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48995: International Search Report and Written Opinion dated Apr. 7, 2010, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.

(56) References Cited

OTHER PUBLICATIONS

U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

\* cited by examiner

POSTURE STATE CLASSIFICATION FOR A MEDICAL DEVICE

RELATED APPLICATIONS

The following application claims priority to provisionally-filed U.S. Patent Application entitled "Posture State Detection System and Method", Patent Application Ser. No. 61/080,049 filed Jul. 11, 2008, which is incorporated herein by reference in its entirety.

The current application includes subject matter related to the following patent applications, which are incorporated herein by reference in their entireties:

'Posture State Classification for a Medical Device', U.S. Publication number 2010/0010380 published Jan. 14, 2010;

'Reorientation of Patient Posture States for Posture-Responsive Therapy', U.S. Publication number 2010/0010383 published Jan. 14, 2010; and 'Posture State Detection Using Selectable System Control Parameters', U.S. Publication number 2010/0010384 published Jan. 14, 2010.

TECHNICAL FIELD

The invention relates to posture detection techniques, and more particularly, to medical devices that detect posture states.

BACKGROUND

A variety of types of medical devices are used for chronic, e.g., long-term, provision of therapy to patients. As examples, pulse generators are used for provision of cardiac pacing and neurostimulation therapies and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY

According to one aspect of the disclosure, techniques are provided for classification of a posture of a patient. Posture classification occurs using a coordinate system of the sensor, which may be an accelerometer, or some other sensor for detecting posture and/or activity. In one embodiment, this posture classification may occur without regard to the coordinate system of the patient's body. As a result, no conversion or transformation need occur to transfer the sensor output signals into a coordinate system of the body. Instead, the sensor output signals may be used as a vector, and directly compared against defined posture definitions. This significantly decreases the time and power expenditure required to classify a patient's posture.

In one embodiment, a sensor, which may include one or more accelerometers, is implanted, or otherwise carried by a patient. The sensor provides a three-dimensional vector indicative of a posture of the patient. As previously stated, this vector may be expressed in the coordinate system of the sensor without regard to the coordinate system of the patient's body. While the sensor is being carried by the patient in a substantially-fixed position, one or more postures may be defined. This may occur by requiring a patient to assume a posture. While the patient is assuming the posture, a corresponding vector may be obtained from the sensor. This vector may be referred to as a defined posture vector. An association is then created between the posture and the defined posture vector.

Next, a user (e.g., a clinician) may select a tolerance for use with the posture under definition. The tolerance describes a relationship to the vector. In one embodiment, this tolerance may describe a cone, a toroid, or some other space surrounding the posture vector. This tolerance is associated with the posture definition.

Any number of posture definitions may be created in the foregoing manner. These posture definitions may then be used to classify a patient's posture. While the sensor is disposed in relation to the patient's body in substantially the same manner as it was carried during the posture definition process, a vector may be obtained from the sensor that is indicative of the patient's current posture. This vector, referred to as a detected posture vector, may be expressed in terms of the coordinate system of the sensor without regard to the coordinate system of the patient's body. As such, this vector may be compared directly to the vectors contained within the posture definitions, and no transformation of the detected posture vector need be performed before the patient's posture may be classified. This greatly improves the efficiency of posture classification, since transforming & the sensor signals to be in a coordinate system of a patient's body is a processing-intensive operation.

According to another aspect, posture classification may be optimized even further by eliminating angle derivations during the posture classification process. Deriving angles is very processing intensive, and therefore is undesirable in applications utilizing limited power resources, such as implantable medical devices. Therefore, non-angular similarities are used to perform posture classification in a manner that saves time and conserves power. In particular, classification of a posture is performed by determining a similarity value ("similarity") between a detected posture vector and a defined posture vector of a defined posture. A similarity value is a value that is not an angle, and does not involve derivation of, or comparisons between, angles. Such a similarity may be expressed as a trigonometric function (e.g., sine or cosine), a Euclidean distance, an absolute distance, a city-block distance, or some other type of non-angular value. If this derived similarity meets the requirements specified by the tolerance for the defined posture, the patient may be classified as being in this posture.

In one embodiment, a similarity between a detected posture vector and a defined posture vector may be based on at least one of a squared length of the defined posture vector and the inner product between the defined posture vector and the detected posture vector. The former value, the squared length of the defined posture vector, is a constant that need be calculated only once after the defined posture vector is selected during the posture definition process. Thereafter, posture classification may be completed using the pre-derived constant and an inner product calculation. This type of processing may be completed very quickly using far fewer processing steps than are needed when angle derivations are used to classify postures.

According to another aspect, the defined posture vectors may be normalized with respect to one another. This involves dividing each defined posture vector by its own length and then multiplying the result by a predetermined scale factor S. All defined posture vectors are thereby normalized to a same known length. In some cases, this allows comparisons between defined posture vectors and a detected posture vector to be completed more efficiently. For instance, this allows inner products to be used to determine to which defined posture vector a detected posture vector is closest, with the outcome being used to classify the patient's posture.

Another aspect of the disclosure relates to using relationships between multiple regions in space to create a single posture definition. These multiple regions in space may be interrelated by a logic functions (e.g., a Boolean-type AND, OR, NOT, etc). As a specific example, a toroid surrounding an Upright vector may be used to define a posture corresponding generally to a patient in a prone position. In addition, multiple cones may be defined, each corresponding to a specific posture a patient may assume while in a prone state (e.g., Face Up, Face Down, Right Side, Left Side, etc.). A definition may then be created for a Lying Down posture that references the space within the toroid and/or the space within each of these cones. This definition thereby combines the various regions in space (toroid and cones) using a logical OR-type function. Any number of regions in space may be combined or otherwise interrelated in a similar manner using other logic functions. For instance, the portion of multiple cones and/or toroids that overlap one another may be referenced using a logical AND-type, NOT-type, or other logical function. This provides a very flexible way to define various postures that may involve multiple regions in space.

Yet another aspect of the disclosure relates to using one or more defined posture vectors to generate virtual posture vectors. As an example of generating a virtual posture vector, consider multiple postures that a patient may occupy while in the prone position. Such postures may include the Face Up, Face Down, Right Side, and Left Side postures. Each such posture may be associated with a defined posture vector that is obtained from a sensor as the patient assumes the posture (e.g., Face Up). The defined posture vectors may be grouped in adjacent pairs, where adjacency refers to how the vectors are positioned in space. For instance, the Face Up and Left Side postures may be used to form an adjacent pair, since these two vectors are "next to" one another in three-dimensional space. Four adjacent pairs may be formed using the four postures of this example. A cross-product may be formed for each adjacent pair, resulting in a vector that is perpendicular to both of the defined posture vectors in the adjacent pair. Assuming all such cross-products are generated with the right-hand rule in mind so that the resulting vectors all have a same sign (positive or negative), these cross-products will all be in a same general direction. An average of these cross-products may be derived for use as a virtual posture vector in detecting a Lying Down posture.

In some cases, a virtual posture vector will result in more accurate posture classification than will an actual defined posture vector. For example, this is true when determining when the patient is lying down. One or more of the positions a patient may typically assume while lying down may involve one portion of the patient's body being elevated above another portion. Thus, many patients occupy a plane that is not perpendicular to, but rather is "skewed" at an angle in relation to, the S-I axis of the patient's body. A virtual vector may be obtained that is substantially perpendicular to this skewed plane. Use of this virtual vector will allow for more accurate detection of a Lying Down posture than will use of an Upright posture vector that substantially coincides with the S-I axis of the body.

According to another aspect of the disclosure, in some cases, it may be advantageous to allow an aspect of the posture definition to be selectable based on evaluation of a condition.

To illustrate the foregoing, consider a patient that may be leaning some distance from a defined posture vector associated with an Upright posture. It may be desirable to allow the patient to lean a significant amount in the forward direction while still allowing the patient to be classified in the Upright posture. In contrast, it may be desirable to allow only a small amount of backward leaning before the patient is re-classified in a posture other than the Upright posture. Because of this asymmetrical requirement, a single tolerance cannot adequately describe the desired relationship to the Upright posture vector. Instead, two different tolerances are needed, with the larger tolerance being associated with leaning forward, and a smaller tolerance being used for leaning backward.

When using the Upright posture definition of the current example to classify a patient's position, it must first be determined whether the patient is leaning forward or backward relative to the Upright posture. To do this, the detected posture vector is compared to two additional defined posture vectors: a posture vector for the Face Down posture (associated with lying face down) and a posture vector for a Face Up (associated with lying face up). Using this comparison, it is determined whether the detected posture vector is closer to the Face Down posture such that the patient is leaning forward, or is instead closer to the Face Up posture such that the patient is leaning backward.

Based on the result of the foregoing evaluation, a tolerance associated with the Upright posture definition may be selected. If the detected posture vector is closer to Face Down, a tolerance describing a larger cone may be selected for use in determining whether the patient is still in the Upright posture. Conversely, if the detected posture vector is closer to Face Up, indicating the patient is leaning backwards, a tolerance describing a smaller cone may be selected for use in determining whether the patient is Upright. In this manner, multiple tolerances, each defining a different region in space, may be associated with a single posture definition. The tolerance to be employed with the definition is selected based on evaluation of a condition.

This is just one example of evaluating conditions to determine an aspect of a posture definition. Other types of conditions may be evaluated. Any number of N comparisons may be performed in the evaluation process, and the result may involve an N-way outcome. The outcome may be used to select size of regions (e.g., size of cones), shape of regions (e.g., cones version toroids), the interrelation of regions (one or more regions, Boolean logic, etc.), and so on.

Other aspects of the current disclosure relate to classifying an activity state of a patient, where an activity state may involve direction of motion (e.g., direction of velocity or direction of acceleration).

An activity state may be defined using patient participation in a manner similar to that described above in reference to creating posture definitions. A patient carrying a sensor may be directed to begin performing an activity (which may involve motion or lack thereof). One or more raw or processed signals indicative of the activity may be obtained from the sensor. In one embodiment, these signals may be obtained from AC components of the sensor signals. These one or more signals may be stored along with the definition of the activity state. A user may supply a tolerance to be used with these signals in much the same way a tolerance is selected for use with a posture vector.

After definition of the activity state, the definition may be used to classify movement of a patient. In this case, one or more signals are received from the sensor while the patient is going about a daily routine. These signals may be processed (e.g., filtered to extract AC signal components, etc.) to obtain a detected activity vector (e.g., velocity or acceleration vector). The detected activity vector may be compared to one or more of the defined activity vectors to determine whether the detected activity vector has a relationship to a defined activity vector as determined by an associated tolerance. This comparison may utilize any of the techniques described herein in regards to posture classification. For instance, this comparison may be performed using similarities without the need to calculate angles, since this greatly reduces power requirements. This comparison may further utilize constants stored with the defined activity state to further reduce calculations. Such constants may include, for instance, a squared length of the defined activity vector in the manner described above.

Any of the processing efficiencies described above in relation to postures may be employed with activity states. For instance, multiple regions in space may be referenced within a single activity state definition. Such regions may be interrelated via Boolean logic operators. Activity state definition may reference virtual activity vectors, wherein such virtual vectors are derived by applying processing steps to multiple defined activity vectors. Processing may, in one embodiment, involve obtaining an average of the cross-products of adjacent pairs of defined activity vectors. These virtual vectors may be used to create activity state definitions in any of the ways described above with respect to posture definitions.

As yet another example, a condition may be associated with an activity state definition. Evaluation of this condition is performed to select some aspect of the activity state definition. For instance, in one example, the evaluation of the condition produces a result that is used to select a size or shape of a region that surrounds a vector that is referenced by the definition.

Posture definitions and activity state definitions may be used together to classify a patient's posture state. Posture state definitions may be created for a patient that reference at least one of a posture definition and an activity state. That is, a patient may be classified in a particular posture state based solely on posture, solely on activity state, or both. Classification of posture and activity state may occur according to any of the techniques described above. This posture state classification may be used to initiate various types of responses. For instance, when a posture state change is detected, a system may automatically modify a therapy that is currently being delivered, select a new therapy for delivery to the patient and/or stop delivery of an existing therapy. In another embodiment, the detected posture state transition may be used to prompt issuance of a notification or to initiate the recording of some information.

According to one aspect, a method of classifying a posture state of a patient is provided. This method includes obtaining a defined vector from at least one sensor disposed in a substantially fixed manner relative to the patient, the defined vector being described in a coordinate system of the at least one sensor and without regard to an orientation in which the sensor is disposed in relation to the patient. This method further includes obtaining a detected vector from the at least one sensor, the detected vector being described using the coordinate system of the at least one sensor and being indicative of the posture state of the patient. The detected vector and the defined vector are compared, and the posture state of the patient is classified based on the comparison and without regard to the orientation in which the sensor is disposed in relation to the patient. An action is initiated via a medical device that is related to providing care for the patient. This action, which is based on the posture state classification, may relate to adjusting therapy, starting or stopping therapy, providing a notification, storing data for analyzing the system or diagnosing the patient, and so on.

According to another aspect, an implantable medical device is disclosed to determine a posture state of a patient. The device includes a sensor substantially fixed to the patient without regard to sensor orientation. A storage device is provided to store at least one posture state definition referencing at least one defined vector expressed in a coordinate system of the sensor. A processor is provided to obtain from the sensor a detected vector in the coordinate system of the sensor, to compare the detected vector to the at least one defined vector and to classify a posture state of the patient based on the comparison and without regard to sensor orientation.

Another embodiment relates to a method including receiving a defined vector from at least one sensor carried in any orientation within a patient, the defined vector being expressed in a coordinate system of the at least one sensor and without regard to the coordinate system of the patient. The method also includes defining a posture state in reference to the defined vector, and obtaining a detected vector from the at least one sensor communicatively coupled to an implantable medical device, the detected vector being expressed in the coordinate system of the at least one sensor and without regard to the coordinate system of the patient. The posture state of the patient is classified based on a comparison between the detected vector and the defined vector. Therapy is delivered to the patient via the implantable medical device based on the posture state classification.

In another embodiment, a storage medium is provided that stores executable instructions to cause a processor to perform a method comprising obtaining a detected vector that is derived from signals of a sensor that is carried in any orientation relative to a patient, the detected vector being indicated in a coordinate system of the sensor. The method further includes obtaining one or more posture state definitions that reference one or more defined vectors, each defined vector being indicated in the coordinate system of the sensor. The detected vector is compared directly to the one or more defined vectors, and the patient's posture state is classified based on this comparison.

The details of one or more embodiments of the disclosed techniques are set forth in the accompanying drawings and the description below. Other features, objects, and advantages of the disclosed mechanisms will be apparent from the description and drawings, and from the claims.

DETAILED DESCRIPTION

Techniques described herein relate to classification of a patient's posture state. Such a posture state may involve at least one of a posture and an activity. Classification of a patient's posture state may then be used to initiate a response. For instance, such classification may be used to deliver therapy in a closed-loop manner.

Examples of therapies that may be delivered in a closed-loop manner using techniques presented in the current disclosure include electrical stimulation or the delivery of therapeutic agents. Electrical stimulation may be, for example, used to treat patients that suffer from chronic back pain, leg pain, or other pain that cannot be treated through other methods. As a patient changes posture state, which may involve changes in position and/or activity, the stimulation may need to be adjusted in order to maintain efficacy. Such changes in a patient's posture state may be detected, classified, and used to modify a therapy that is currently being delivered, or to select a new therapy for delivery to the patient. In another embodiment, the detected posture state transition may be used to prompt some notification, or to record some information.

According to some embodiments of the disclosure, a medical device, e.g., an implantable medical device (IMD) includes or is coupled to a sensor that senses a posture state. The sensor may be a three-axis accelerometer such as a piezoelectric and/or micro-electro-mechanical (MEMs) accelerometer. The sensed posture state may then be used to initiate some action, which may be an action to be taken in regards to the patient. This action may merely involve storing the sensed posture state. The action may additionally or alternatively involve a change in delivered therapy, providing a notification, and/or any other action that is usefully taken in regards to the sensed posture state.

The IMD may store a table or other data structure that contains records. Each such record may contain therapy information associated with a respective posture state. The IMD may automatically sense the current posture state of the patient and/or changes in the posture state of the patient. This sensed information may be employed to reference the table or other data structure that contains the therapy information. An appropriate therapy may thereby be selected that provides the most efficacious results for the patient's current posture state.

Figure 1:
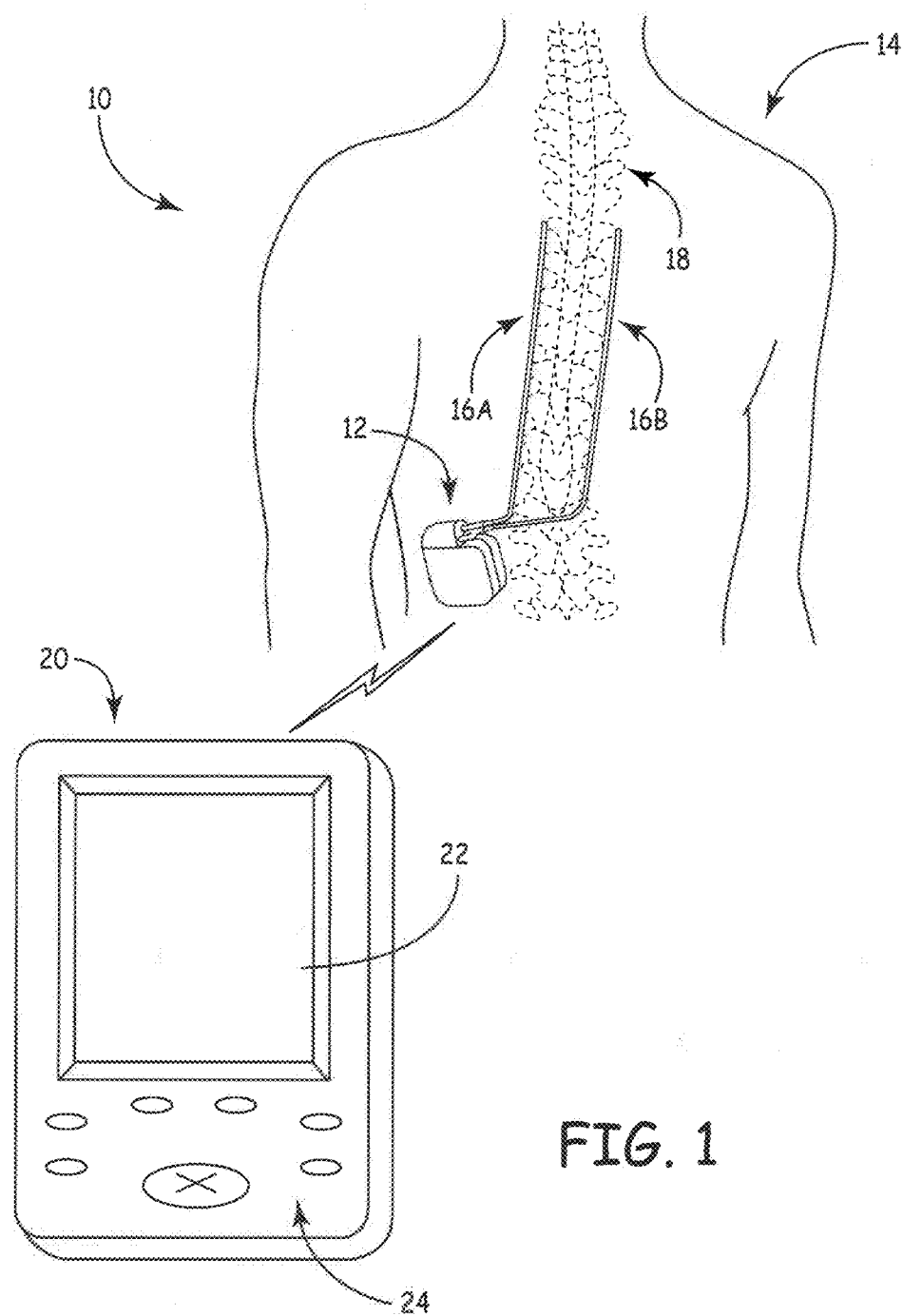
FIG. 1 is a conceptual diagram illustrating an example system that facilitates the definition and classification of posture states according to the disclosure.

FIG. 1 is a conceptual diagram illustrating an example system 10 that facilitates the definition and classification of posture states according to the disclosure. In the illustrated example, system 10 includes an IMD 12, which is implanted within a patient 14, and delivers neurostimulation therapy to patient 14.

IMD 12 delivers neurostimulation therapy to patient 14 via therapy connections 16A and 16B ("therapy connections 16"), which may be leads carrying electrodes, for instance. In this type of application, the electrodes (not shown) may be, e.g., electrode pads on a paddle lead, circular (e.g., ring) electrodes surrounding the body of leads, conformable electrodes, cuff electrodes, segmented electrodes, or any other type of electrodes capable of forming unipolar, bipolar or multipolar electrode configurations for therapy. In some applications, such as SCS to treat chronic pain, the adjacent therapy connections 16 may have longitudinal axes that are substantially parallel to one another, and one therapy connection need not have the same number of electrodes as another therapy connection.

More than two, or only one, of the therapy connections 16 may be provided by the system. In one case, three therapy connections 16 may be provided, each carrying electrodes to form a so-called 4-8-4 or 4-16-4 lead configuration, whereby the numbers indicate the number of electrodes in a particular column, which can be defined by a single lead. Other lead configurations, such as 8-16-8, 8-4-8, 16-8-16, 16-4-16, are also possible. External programmer 20 may be initially told the number and configuration of leads 16 in order to appropriately program stimulation therapy.

Therapy connections 16 may, as shown in FIG. 1, be implanted proximate to the spinal cord 18 of patient 14, and IMD 12 may deliver SCS therapy to patient 14 in order to, for example, reduce pain experienced by patient 14. However, the disclosure is not limited to the configuration of therapy connections 16 shown in FIG. 1 or the delivery of SCS therapy. For example, one or more therapy connections 16 may extend from IMD 12 to the brain (not shown) of patient 14, and IMD 12 may deliver deep brain stimulation (DBS) therapy to patient 14 to, for example, treat tremor, Parkinson's disease, or epilepsy.

As further examples, one or more therapy connections 16 may be implanted proximate to the pelvic nerves, stomach, or other organs (not shown) and IMD 12 may deliver neurostimulation therapy to treat incontinence, gastroparesis, sexual dysfunction or other disorders. Additionally, this disclosure is not limited to implantable devices. Any external medical device may classify posture states for use in delivering therapy according to the techniques of the disclosure.

Further, as discussed above, the disclosure is not limited to embodiments in which IMD 12 delivers stimulation therapy. For example, in some embodiments, IMD 12 may additionally or alternatively be coupled to one or more catheters or other substance delivery devices to deliver one or more therapeutic substances to patient 14, e.g., one or more drugs. Example therapeutic agents that IMD 12 may deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics. In this case, IMD 12 functions as a drug pump and communicates with external programmer 20 to initialize therapy or modify therapy during operation. In addition, IMD 12 may be refillable to allow chronic drug delivery.

When IMD 12 delivers a therapeutic substance to the patient, multiple therapy connections 16 such as catheters may be located to deliver the substance to the same anatomical location or the same tissue or organ. Alternatively, each catheter may deliver therapy to different tissues within patient 14 for the purpose of treating multiple symptoms or conditions. In some embodiments, IMD 12 may be an external device which includes a percutaneous catheter that provides one of therapy connections 16 or that is coupled to therapy connections 16, e.g., via a fluid coupler. In other embodiments, IMD 12 may be coupled to therapy connections 16 that provide both electrical stimulation and drug delivery therapy.

Although the target therapy delivery site may be proximate to spinal cord 18 of patient 14, other applications are possible. For instance, the target delivery site in other applications of drug delivery system may be located within patient 14 proximate to, e.g., sacral nerves (e.g., the S2, S3, or S4 sacral nerves) or any other suitable nerve, organ, muscle or muscle group in patient 14, which may be selected based on, for example, a patient condition. In one such application, drug delivery system may be used to deliver a therapeutic agent to tissue proximate to a pudendal nerve, a perineal nerve or other areas of the nervous system, in which cases, therapy connections 16 would be implanted and substantially fixed proximate to the respective nerve. Thus, many types of applications are possible.

Also, in some aspects, techniques for evaluating postures and posture states as described herein may be applied to IMDs that are generally dedicated to sensing or monitoring and do not include stimulation or other therapy components. For instance, the posture state classification mechanisms described herein may be used for diagnostic purposes, such as diagnosing a need for therapy, or determining how a patient is responding to existing therapy. Posture state classification may also be used to provide notifications, such as providing notification via a wireless link to a care giver that a patient has potentially experienced a fall. Thus, posture definition and classification according to the current disclosure may be used to initiate many types of actions, including storing the classification for later analysis, initiating a change in therapy, prompting a notification, and so on.

In exemplary embodiments, IMD 12 performs various operations, including posture state classification, under the control of one or more programs. A program includes one or more parameters that define an aspect of posture classification and/or detection according to that program.

In exemplary embodiments, IMD 12 may initiate actions in response to information within a record. For instance, a plurality of records may be stored in a table or other data structure. Each such record may describe at least one posture state and an associated action that is to be taken in response to detection of this posture state. As discussed above, a posture state is determined based on at least one of a defined posture and a value for an activity parameter (a parameter indicative of overall patient activity, for instance). When IMD 12 detects a posture state, IMD 12 may initiate the action that is indicated by the information in the record for that posture state. This action may involve delivery of therapy according to a particular program, group of programs and/or a set of parameters. This action may alternatively or additionally involve providing some notification and/or recording some information.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a clinician programmer used by a clinician to define postures and posture states according to the current disclosure. The defined postures may then be used to detect postures and posture states that are assumed by the patient during daily life. The detected postures may be used to determine a type of therapy to provide to the patient, to monitor general well-being of the patient, to prescribe new therapies for the patient, and to determine whether the patient has undergone a posture-specific event such as suffering a fall.

Figure 2:
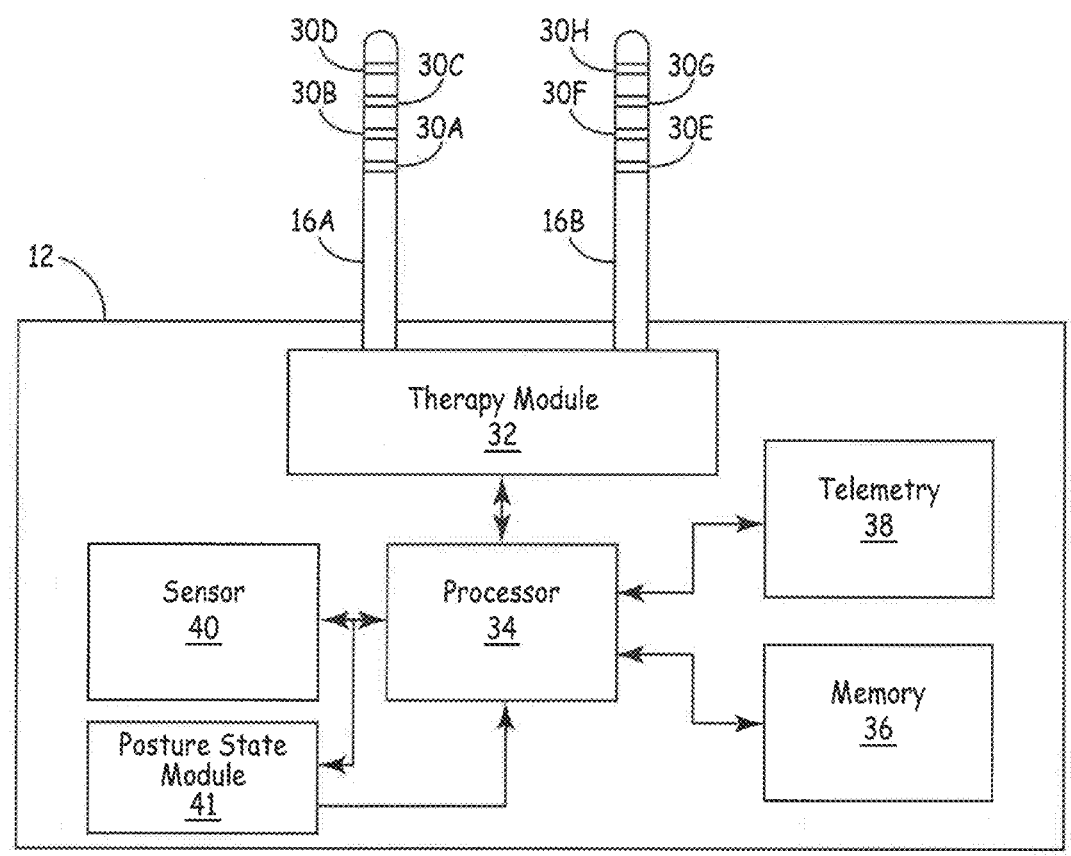
FIG. 2 is a block diagram illustrating one embodiment of an implantable medical device in greater detail.

FIG. 2 is a block diagram illustrating one embodiment of IMD 12 in greater detail. IMD 12 may deliver neurostimulation therapy via therapy connections 16A and 16B. As discussed above, these therapy connections may be leads having one or more electrodes 30A-H (collectively "electrodes 30") or some other therapy mechanism, such as one or more catheters for delivering a substance to a patient. IMD 12 may be coupled to any number of therapy connections.

Therapy connections 16A and 16B are coupled to IMD 12 via therapy module 32. This may be a stimulation pulse generator, for example. Such a pulse generator may be coupled to a power source such as a battery. Therapy module 32 may deliver electrical pulses to patient 14 and/or may deliver some type of substance, such as a drug.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with the amplitudes and widths, and at the rates specified by the program. Processor 34 may also control therapy module 32 to deliver such pulses via a selected subset of electrodes 30 with selected polarities, e.g., a selected electrode configuration, as specified by the program.

IMD 12 also includes a telemetry circuit 38 that allows processor 34 to communicate with programming device 20. For example, a clinician may select programs, parameters, posture definitions, posture state definitions, and associated therapies and actions that are to be transferred to memory 36 of IMD 12. Processor 34 also communicates with programming device 20 to provide diagnostic information stored in memory 36 to a clinician via telemetry circuit 38. Processor 34 may also communicate with a patient programming device to receive from a user such as patient 14 therapy parameter adjustments or other therapy adjustments, as well as commands to initiate or terminate stimulation. Telemetry circuit 38 may correspond to any telemetry circuit known in the implantable medical device arts.

IMD 12 further includes a sensor 40 to sense one or more parameters used to detect a posture state. In exemplary embodiments, sensor 40 includes a three-axis accelerometer, such as a piezoelectric and/or MEMs accelerometer. In other embodiments, multiple single or multi-axis accelerometers may be employed in place of one three-axis accelerometer. In yet other examples, sensor 40 may include gyroscopes or other sensors capable of sensing posture and/or activity levels. Thus, it will be understood that sensor 40 may comprise more than one sensor.

In exemplary embodiments, sensor 40 is located within a housing (not shown) of IMD 12. However, the disclosure is not so limited. In some embodiments, sensor 40 is coupled to IMD 12 via additional therapy connections 16 (not shown). The sensor may be located anywhere within patient 14.

In alternative examples, first and second sensors may be located in different positions within patient 14 and relative to components of IMD 12. For example, one posture sensor may be an independent implantable sensor that is implanted adjacent but physically disconnected from IMD 12. Another sensor may be, e.g., connected to an additional sensor lead positioned within patient 14 adjacent therapy connections 16. Alternatively, the other sensor may be an independent implantable sensor that is implanted adjacent but physically disconnected from therapy connections. In some examples, one posture sensor is arranged proximate a therapy delivery site within patient 14, while another sensor is arranged closer to IMD 12 than the first sensor.

In some embodiments, IMD 12 may be coupled to one or more accelerometers or other position sensors located at various positions on the external surface of patient 14. In yet other embodiments, these one or more sensors may communicate wirelessly with IMD 12 instead of requiring one or more leads to communicate with the IMD. For example, sensor 40 may be located external to patient 14 and may communicate wirelessly with processor 34, either directly or via programming device 20.

As previously mentioned, sensor 40 senses one or more parameters that are used to detect a posture state. A posture state is a state that is classified by at least one of a posture definition and an activity state, where the activity state may describe, for example, an overall activity level, an activity level in one or more selected directions, a vector associated with velocity or acceleration, and so on.

Example posture states that may be detected include an Upright posture state. This posture state may be defined as that occurring when the patient is in an upright posture without regard to an activity state. As another example, an Upright and Active posture state may be associated with an upright posture and an activity state that is associated with an activity level above some predetermined threshold level. Additional exemplary posture states such as "Running", "Sitting", "Bending Over", and so on, may be defined and subsequently sensed by sensor 40.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as random access memory (RAM), read-only memory (ROM), non-volatile RAM (NVRAM), electrically-erasable programmable ROM (EEPROM), flash memory, and the like.

FIG. 2 further includes posture state module 41. This posture state module is provided in one embodiment to process the analog output of sensor 40. Posture state module 41 may include discrete components, a microprocessor, a controller, a digital signal processor (DSP), an application specific integrated circuit (ASIC), a field-programmable gate array (FPGA), and/or the like. Posture state module 41 may operate alone, or in conjunction with processor 34, to process the sensor output for use in detecting a posture state. As an example, posture state module 41 may process the raw signals provided by sensor 40 to determine activity counts indicative of activity level, velocity along one or more accelerometer axis (as may be obtained by integrating the respective accelerometer signal), and so on, for use in detecting a posture state. This is discussed further below.

In other embodiments, posture state module 41 may additionally or alternatively be configured to sense one or more physiological parameters of patient 14. For example, physiological parameters may include heart rate, electromyography (EMG), an electroencephalogram (EEG), an electrocardiogram (ECG), temperature, respiration rate, or pH. These physiological parameters may be used by processor 34, in some embodiments, to confirm or reject changes in sensed posture state that may result from vibration, patient travel (e.g., in an aircraft, car or train), or some other false positive posture state detection by posture state module 41.

Figure 3:
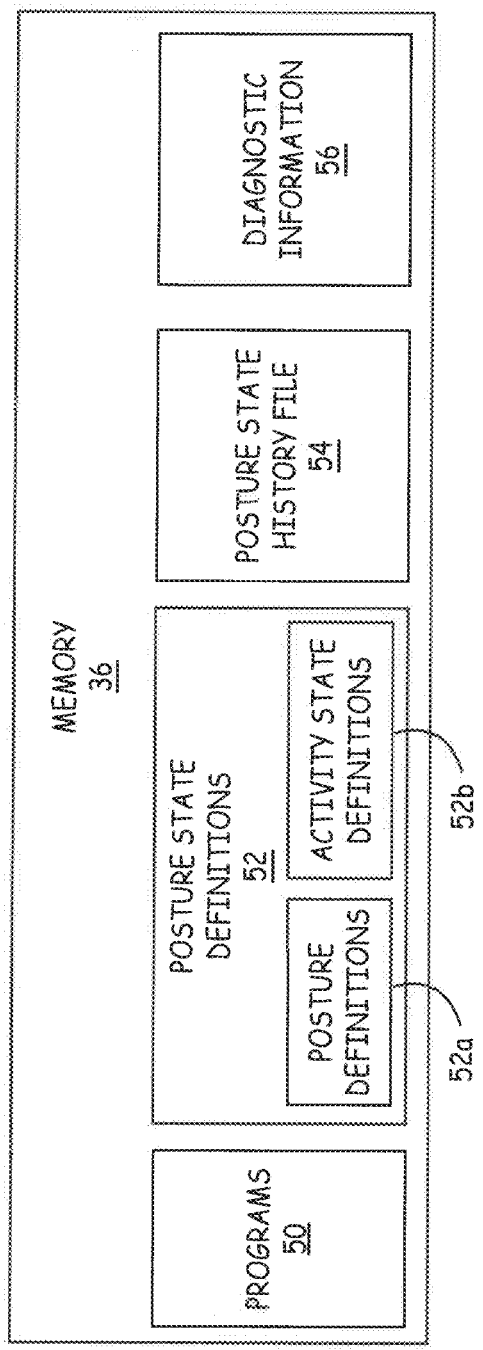
FIG. 3 is a block diagram illustrating an exemplary configuration of a memory of an implantable medical device according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to create posture state definitions 52. As discussed above, each posture state definition 52 is associated with at least one of a posture definition 52a and an activity state definition 52b.

A patient's posture, activity state, and/or posture state may be recorded in a posture state history file 54. This file may record, for instance, the patient's current posture information, including current posture and activity states as well as previous posture and activity states assumed by the patient over some period of time.

Memory 36 may also store diagnostic information 56 for use in determining how a patient is responding to therapy, whether therapy modification is needed, whether therapy is to be initiated, and so on.

In some cases, posture state information may be communicated to an external device such as an external monitor which is used to track a patient's condition. Alerts may also be transmitted in this manner. For example, a warning may be transmitted indicating the patient has potentially taken a fall.

As discussed above, the signals of sensor 40 are used to detect a posture. For purposes of this discussion, it will be assumed sensor 40 is a three-axis accelerometer, although sensor 40 could comprise multiple single-axis accelerometers instead. Sensor 40 provides a respective signal describing acceleration along each of the x, y, and z axis. These axes will be assumed to be orthogonal.

Each of the x-, y-, and z-axis signals provided by sensor 40 has both a DC component and an AC component. The DC components describe the gravitational force exerted upon the sensor, and can thereby be used to determine orientation of the sensor within the gravitational field of the earth. According to the current disclosure, the orientation of the sensor remains relatively fixed with respect to the patient such that the DC components of the x, y and z signals may be utilized to determine the patient's orientation within the gravitational field, and to thereby determine the posture of the patient.

Prior art mechanisms generally utilize a patient's body coordinate system when determining posture. A body coordinate system may include the superior-inferior (S-I) body axis (extending toe to head), the anterior-posterior (A-P) body axis (extending back to front), and the lateral-medial (L-M) body axis (extending right to left). Postures may be readily defined in terms of these body coordinate axes.

In a simple scenario, a sensor 40 may be positioned within, or on, a patient such that the x, y, and z axes of sensor 40 are aligned with the patient's body coordinate system. In one example, the y axis of sensor 40 may be aligned with the S-I body axis, the z axis of sensor 40 may be aligned with the A-P body axis, and the x axis of sensor 40 may be aligned with L-M body axis. When such an alignment between the sensor coordinate system and body coordinate system can be achieved, the sensor signals may be readily used to detect a posture that is defined in terms of the body coordinate system. However, such alignment may be difficult to achieve and maintain. For instance, sensor position may shift while it is being carried within, or on, the patient.

Another approach to posture classification involves using a correction factor that takes into account that sensor 40 may not be aligned with the body coordinate system. This correction factor, which is used to translate sensor output into the body coordinate system, may be expressed in several ways. For instance, the correction factor may be a transfer matrix that is applied to the sensor output. Alternatively, the correction factor may include pitch, roll and yaw angles that are applied to the sensor signals to perform this translation. Other mechanisms are possible for expressing the correction factor. According to this approach, the sensor signals may only be used to detect posture after the correction factor is applied and the signals have been expressed in terms of the patient's body coordinate system.

Figure 4:
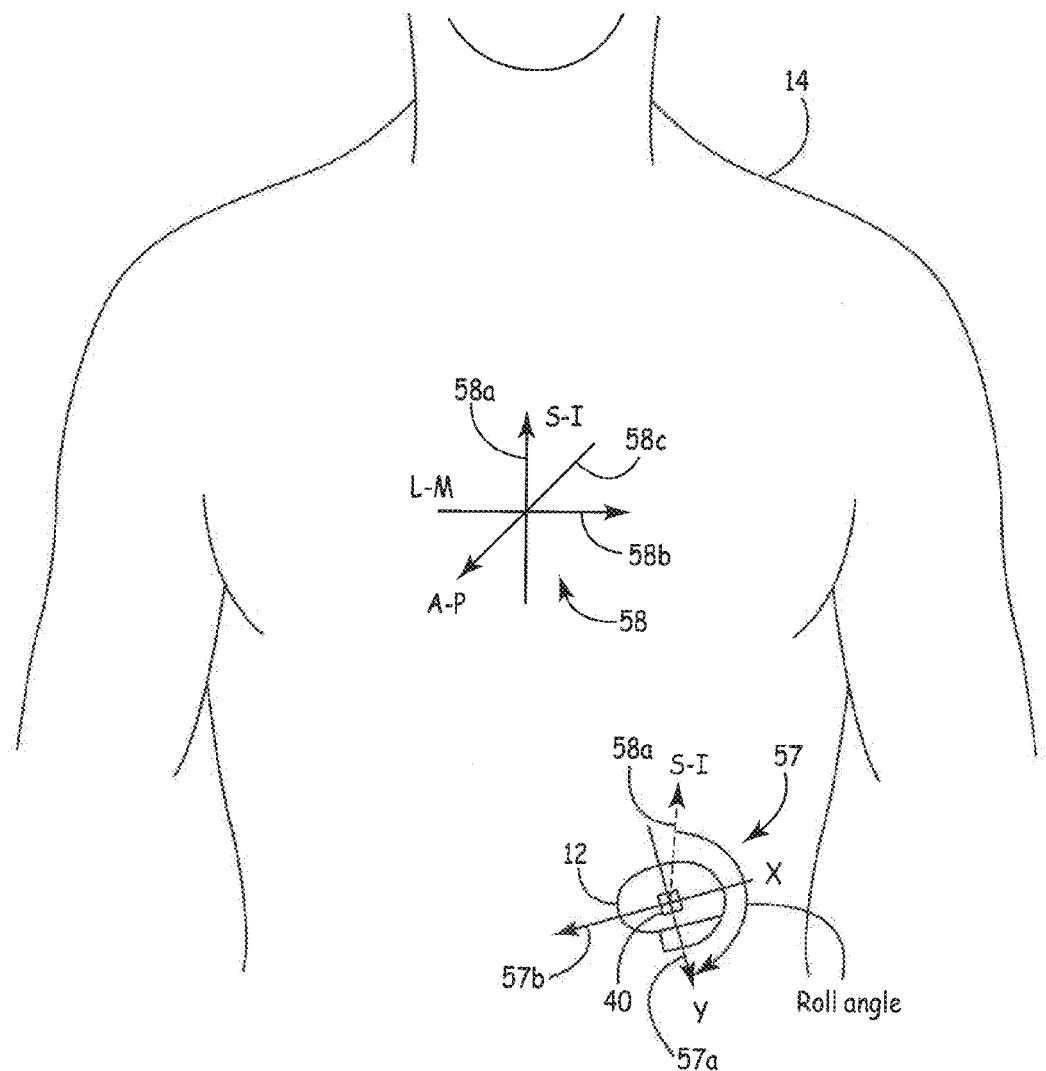
FIG. 4 is a conceptual diagram illustrating use of a correction factor to translate sensor signals from a sensor coordinate system into a body coordinate system.

FIG. 4 illustrates the use of a correction factor to translate sensor signals from a sensor coordinate system into a body coordinate system. IMD 12 is shown implanted within patient 14. As discussed above, sensor 40 is carried inside a housing of IMD 12. Sensor 40 has a sensor coordinate system 57 that includes y axis 57*a*, x axis 57*b*, and z axis (not shown for simplicity.)

Patient 14 has a body coordinate system 58 that includes S-I axis 58*a*, L-M axis 58*b*, and A-P axis 58*c*. This body coordinate system 58 is not aligned with the sensor coordinate system in FIG. 4. For instance, the S-I axis 58*a* does not align with y axis 57*a* of the sensor coordinate system, and the L-M axis 58*b* does not align with the x axis 57*b* of the sensor coordinate system. Therefore, the output of sensor 40 cannot be used to directly detect postures that are defined in terms of the body coordinate system.

Before the output of sensor 40 can be used to detect postures defined in terms of the body coordinate system, a correction factor must be applied to the sensor output. In this example the correction factor includes the roll angle 59. The roll angle describes the misalignment of the S-I axis 58*a* and the y axis 57*a* of sensor 40. Similar angles may be used to describe any misalignment between the L-M axis 58*b* and the x axis 57*b*, and any misalignment between the A-P axis 58*c* and the z axis (not shown) of the sensor 40. Mechanisms for applying correction factors are provided, for example, in commonly-assigned U.S. Pat. No. 6,044,297 entitled "Posture and Device Orientation and Calibration for Implantable Medical Devices".

This application of the correction factor to a sensor output may be processing intensive. Moreover, the correction factors must be initially determined. In an IMD that will perform posture classification on a regular basis, it may be desirable to eliminate these steps to conserve power.

According to some embodiments of the disclosed posture detection mechanism, the current techniques may define postures in the coordinate system of the sensor rather than in the patient's body coordinate system. Therefore, there is no correction factor that need be applied to the output of sensor 40. Moreover, the correction factors do not need to be derived. This dramatically simplifies the process of performing posture detection, and thereby saves a significant amount of power and processing time. This is particularly important for devices such as IMDs that have a limited power supply which may involve rechargeable or non-rechargeable batteries.

To define postures in the coordinate system of the sensor, sensor 40 is positioned on, or in, patient 14 in any orientation in a substantially fixed manner. For instance, the sensor may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensor relative to the patient is substantially unchanging, at least over some period of time during which posture classification will occur.

Once the sensor is disposed in relation to the patient's body, the patient is asked to temporarily assume a posture. Outputs from sensor 40 are obtained while the patient is in the assumed posture. In the case of a three-axis accelerometer, these outputs define a vector in three-dimensional space that may, in one embodiment, be expressed in terms of the coordinate system of sensor 40 without regard to the coordinate system of the patient's body. This vector that is defined by the output of sensor 40 may be any vector in three-dimensional space.

Next, the vector, which may be referred to as a defined posture vector, is associated with the posture that the patient has been asked to assume. This association may occur by storing the defined posture vector or some representation thereof with a designation that identifies the posture. Such an association may be stored within a table, data structure, or other organized aggregation of the data shown as posture definitions 52a of FIG. 3.

The patient may be asked to assume any number of postures in the foregoing manner. As each posture is assumed, signals are obtained from sensor 40 that are indicative of a defined posture vector that are, in one embodiment, expressed in the coordinate system of sensor 40 without regard to the coordinate system of the patient. The defined posture vector or a representation thereof is associated with the posture under definition.

After a defined posture vector is associated with a posture, a tolerance may be selected. This tolerance defines a relationship to the defined posture vector. This relationship may define a cone, a toroid, or some other region that surrounds or is otherwise disposed in relation to the posture vector, as will be disclosed below in reference to the remaining figures. Like the defined posture vector, this selected tolerance is associated with the posture. Together, the defined posture vector and the tolerance will be used to determine whether a patient has assumed the associated posture.

A patient may use a programming device such as clinician programming device 20 to define a posture. For instance, a user may issue a command via programming device 20 to IMD 12 when a patient has assumed a desired position. This command causes IMD 12 to obtain signal values from sensor 40, which are optionally processed by posture state module 41 of IMD and stored in memory 36. These sensor signals may also be uplinked via telemetry circuitry 38 to an external device such as programming device 20 to undergo some of the processing steps. The captured sensor signals may be associated with an indication (e.g., an alpha-numeric tag, a binary tag, etc.) identifying a posture as specified by a user employing programming device 20. Such an indication may be provided using display 22, keypad 24, a touch screen, a peripheral pointing device, and/or other types of user interface mechanisms, as described above. A user interface such as a graphical user interface may be employed during this process. A tolerance may likewise be specified by the user for association with this posture definition. The associations may be stored in memory of programming device 20, in memory 36 of IMD 12, or in some other storage facility. Techniques for defining a posture vector and creating the above-described associations are discussed further below.

In the foregoing manner, one or more postures are defined. Each posture is associated with a vector and a tolerance. These defined postures may then be used to classify a patient's positions and movements. As may be appreciated, during this classification process, it is important that sensor 40 be maintained in substantially the same position relative to the patient as existed when the posture definitions were originally obtained. This will allow the same sensor coordinate system that was used to define the postures to likewise be used to classify a patient's positions. If the sensor orientation relative to the patient changes, as may occur if an IMD 12 rotates with respect to patient 14, recalibration of the defined postures must be performed. This will involve again obtaining and re-recording vectors associated with each defined posture in the coordinate system of sensor 40. After being created in any of the above-described ways, posture definitions may be used to classify a posture of a patient as follows. As a patient moves and/or assumes a posture, outputs from sensor 40 are processed by posture state module 41 to obtain measurements that define a detected posture vector. In one embodiment, this detected posture vector, like the defined posture vector, is expressed in terms of the sensor coordinate system without regard to the patient coordinate system. For this reason, the detected posture vector may be compared directly to one or more of the defined posture vectors without the need to apply a correction factor to the detected posture vector. This comparison indicates whether the detected posture vector has a relationship to any of the defined posture vectors that is specified by an associated tolerance. For instance, assume a tolerance describes a cone surrounding a defined posture vector and indicates that the detected posture vector must lie within the cone to satisfy the requirements of the definition. The comparison step will determine whether the detected posture vector lies within the cone.

As previously mentioned, if the detected posture vector and the defined posture vectors are expressed in terms of the sensor coordinate system without regard to the patient coordinate system, this classification step does not involve applying any correction factor to the detected posture vector. A direct comparison may be performed between the detected and the defined posture vectors because both vectors are described in terms of the sensor coordinate system. This comparison may be completed in a manner that is not processing intensive.

Figure 5A:
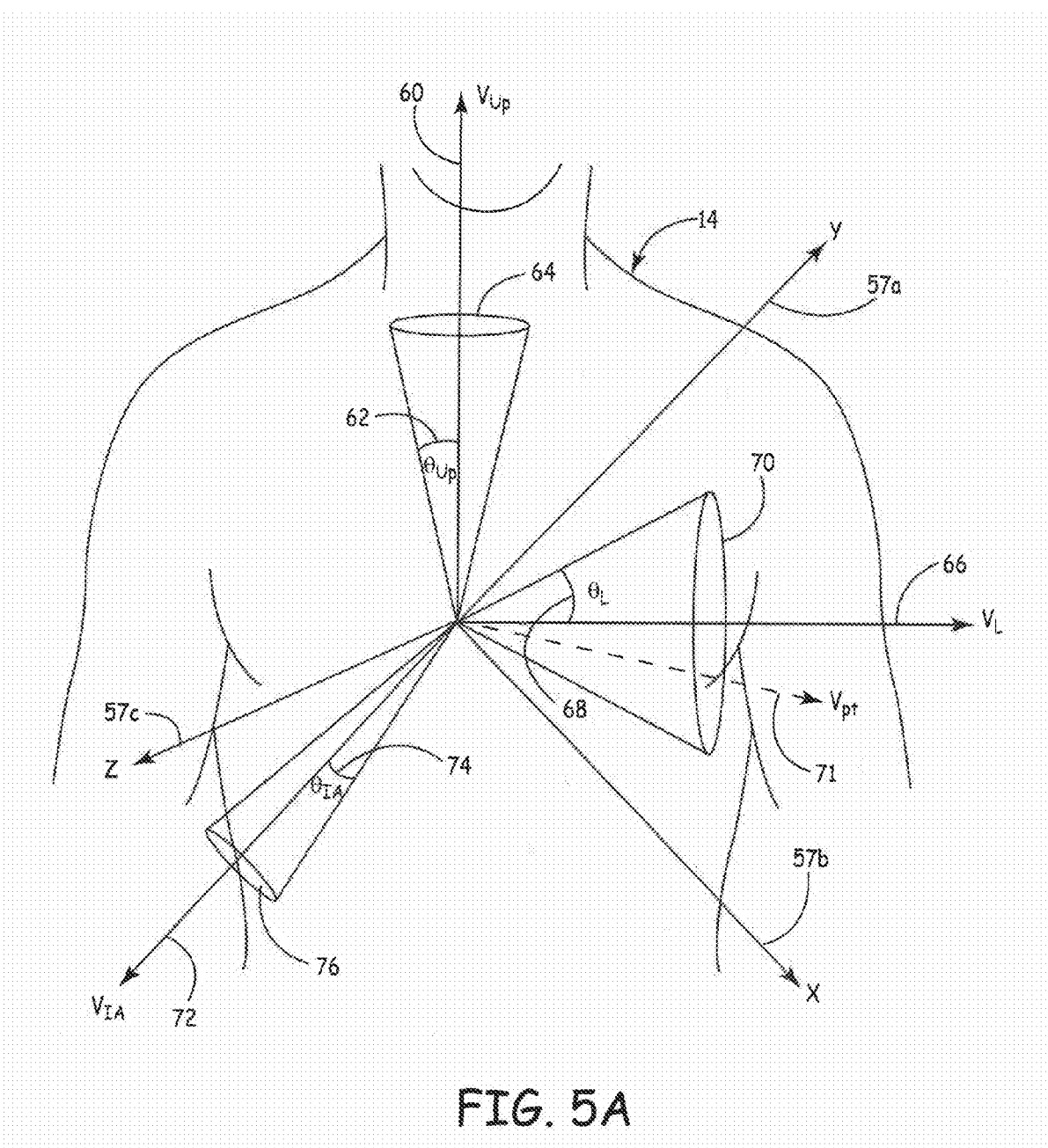
FIG. 5A is a graph illustrating exemplary methods of defining postures according to one embodiment of the disclosure.

FIG. 5A is a three dimensional graph illustrating one method of defining postures using sensor 40. Sensor 40 (not shown) is disposed in a substantially fixed manner relative to patient 14. The coordinate system of sensor 40 includes y axis 57a, x axis 57b, and z axis 57c. As described previously, in one embodiment, this sensor coordinate system need not be orientated in any particular manner relative to patient 14 or the patient's body coordinate system 58 (FIG. 4).

When patient is known to be standing upright, sensor 40 will provide outputs that can be processed to obtain a vector $[V_1, V_2, V_3]$ which is shown as $V_{Up}$ 60. For purposes of this disclosure, this vector and similar vectors are described using a notation wherein the first vector component (e.g., $V_1$) may correspond to an x-axis component of the vector, the second vector component (e.g., $V_2$) may correspond to a y-axis component of the vector, and the third vector component (e.g., $V_3$) may correspond to a z-axis component of the vector.

Vector $[V_1, V_2, V_3]$ may be associated with an Upright posture, as by storing some indication of this posture along with one or more values identifying the vector. A tolerance may then be selected for this posture that describes a relationship to vector $V_{Up}$. In the current example, the tolerance relates to a cone 64 defined by an angle $\theta_{Up}$ 62, wherein $\theta_{Up}$ may be a deflection angle. For purposes of this posture definition, the cone identifies a maximum distance from vector $V_{Up}$. So long as a patient's detected posture vector lies within this cone, the patient will be considered to be in the Upright posture. Thus, the patient may be leaning slightly forward, backward, or sideways from the vector $V_{Up}$, but may never-the-less be categorized as standing so long as the detected posture vector lies within cone 64.

Posture vector $V_{Up}$ 60, the predetermined angle $\theta_{Up}$ 62, and some description of the relationship to be identified by the tolerance (e.g., "within the cone") may be associated with the Upright posture for use in later classifying a patient's posture. This may involve storing this information as one of posture definitions 52a (FIG. 3) in memory.

In a similar manner, other posture vectors may be defined. For instance, a vector $V_L$ 66 may be defined that will be used to determine a Left Side posture in which the patient 14 will be classified when he is lying on his left side. In a manner similar to that described above, a tolerance is defined for this vector that may involve a cone 70 having a size indicated by angle 68. As with the Upright posture, this cone indicates a maximum distance from $V_L$ 66. When a detected posture vector lies within this posture cone 70, the patient 14 will be classified as lying on his left side. This is the case for detected posture vector $V_{pt}$ 71, which is shown to be within cone 70.

Any other one or more postures may be defined in a similar manner. As one example, a vector $V_{IA}$ 72 may be associated with some posture Inverted Angle, in which a patient may be classified when he is lying face down with his head somewhat below his feet. As was the case above, this example shows a tolerance being selected for this posture that involves a cone 76 defined by angle $\theta_{IA}$ 74. If a detected posture vector lies within this cone, it will be classified as the Inverted Angle posture.

Some space may not be included within any posture definition. For instance, in this illustration, space outside of cones 64, 70 and 76 is excluded from a posture definition. This space represents an unclassified, posture. In one embodiment, if a detected posture vector falls within this space, the patient is categorized as being in an Undefined posture. In another embodiment, when a detected posture vector falls within this space, the patient's posture may remain classified as it was prior to the time the patient's detected posture vector entered this space. For instance, if the patient was previously classified as being in the Upright posture, the patient may still be classified in the Upright posture after the detected posture vector transitions into the space that is not associated with a defined posture. The size of this space associated with the Undefined posture will vary depending on the number of posture definitions in use within the system, as well as the size of the tolerance associated with each posture definition.

According to other scenarios, the posture definitions may not be mutually exclusive. For instance, although none of the areas of cones 64, 70 and 76 overlap in FIG. 5A, overlap of the cones is possible in another embodiment. If such overlap exists, it is possible for a patient to be classified as being in more than one posture. Alternatively, the overlapping cones may be used to define a single posture. These embodiments are described below.

In the foregoing manner, any vector may be selected for use in defining a posture. Each defined posture vector need not be in any particular plane or have any predetermined relationship to any other defined posture vector. As another example, an Upright posture need not be orthogonal to a Lying Down posture. Moreover, postures assumed while the patient is reclining (e.g., Right Side, Left Side, Face Up, Face Down, etc.) need not be co-planar. As still another illustration, a Right Side posture defined to describe a patient lying on his right side need have no particular relationship to the Left Side posture that is discussed in regards to FIG. 5A.

Using the techniques described above, posture definitions may be created that are specific to a particular patient's activities and/or profession. For instance, a bank teller may spend a significant portion of his working day leaning forward at a particular angle. Therefore, sensor 40 may be used to obtain a defined posture vector that is specific to this Leaning posture. Similarly, a tolerance may be selected for this posture definition that is specific to the particular patient. Thereafter, classification of the patient's position in this Leaning posture may be used to trigger delivery of therapy, recordation of patient information and/or some other type of action. As previously discussed, in one embodiment, all defined posture vectors may be defined in the coordinate system of sensor 40 and without regard to a patient's body coordinate system to provide for efficient posture classification.

All of the above examples of posture definitions describe a cone. The size of a cone may be described by an angle of the cone. For instance, the size of cone 64 is described by angle $\theta_{Up}$ 62. While the angles may be selected to be of any size, in one embodiment, angles may be generally between approximately 1 degree and approximately 70 degrees. In other examples, cone angles may be between approximately 10 degrees and approximately 30 degrees. In some examples shown in FIG. 5A, the cone angles are approximately 20 degrees.

Another way to specify a cone is by selecting a radius of a base of a cone relative to a center vector or axis. This radius may, but need not, be symmetrical about the associated defined posture vector. In the example shown in FIG. 5A, cones 64, 70, and 76 each has rotational symmetry about the respective center axis 60, 66, and 72. Thus, FIG. 5A illustrates cones in which center lines 60, 66, and 72 pass perpendicularly through the centers of the respective base. In other examples, center lines 60, 66, 72 may not pass perpendicularly through the centers of the respective base. Thus, cones that are referenced by the posture definitions may be described and configured in multiple ways.

When posture definitions reference cones, the patient may be classified as occupying the associated posture if a sensor reading provides a detected posture vector that is within the cone (i.e., the detected posture vector is no more than the maximum distance described by the cone from the defined posture vector). However, this need not be the case, and the patient may instead be classified as occupying an associated posture if a sensor reading is outside of a cone, as described in reference to FIG. 5B.

Figure 5B:
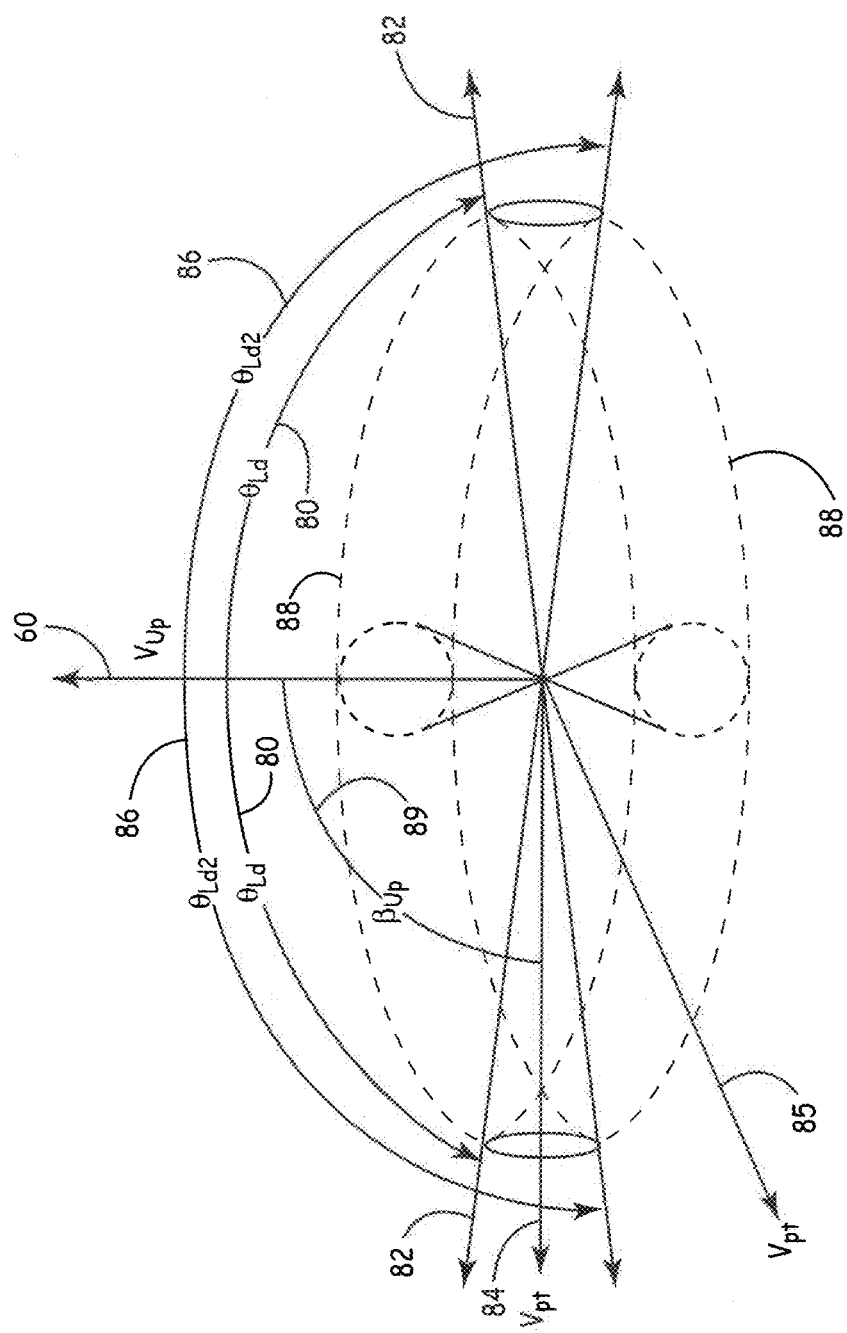
FIG. 5B is a graph illustrating exemplary methods of defining a Lying Down posture according to another embodiment of the disclosure.

FIG. 5B is a graph illustrating another relationship that may be used to create posture definitions. A posture may be defined using vector $V_{Up}$ 60 and an angle $\theta_{Ld}$ 80 that defines a minimum (rather than a maximum) distance from vector $V_{Up}$ 60. A patient may be classified as occupying this posture if the detected posture vector is farther away from the defined posture vector $V_{Up}$ 60 than the angle $\theta_{Ld}$ 80 (i.e., lies outside of a cone 82). This type of definition may be used to define a Lying Down posture, for instance. According to this example, both of detected posture vectors $V_{pt}$ 84 and $V_{pt}$ 85 will be classified as being in this Lying Down posture since both vectors are outside of cone 82 that surrounds $V_{Up}$ 60.

In yet another example of a posture definition, two angles, $\theta_{Ld}$ 80 and $\theta_{Ld2}$ 86, may be used in conjunction with the defined posture vector $V_{Up}$ 60 to express a tolerance. For example, these two angles may be selected to describe a toroid 88 (shown dashed) that surrounds the posture vector $V_{Up}$. A patient may be classified as occupying the defined posture if the detected posture vector lies within this toroid. In this case, a patient associated with detected posture vector $V_{pt}$ 84 is classified as being in the Lying Down posture since this posture vector lies within toroid 88. However, a patient associated with vector $V_{pt}$ 85 is not classified as being in the Lying Down posture, since this detected posture vector is outside of toroid 88.

Figure 6:
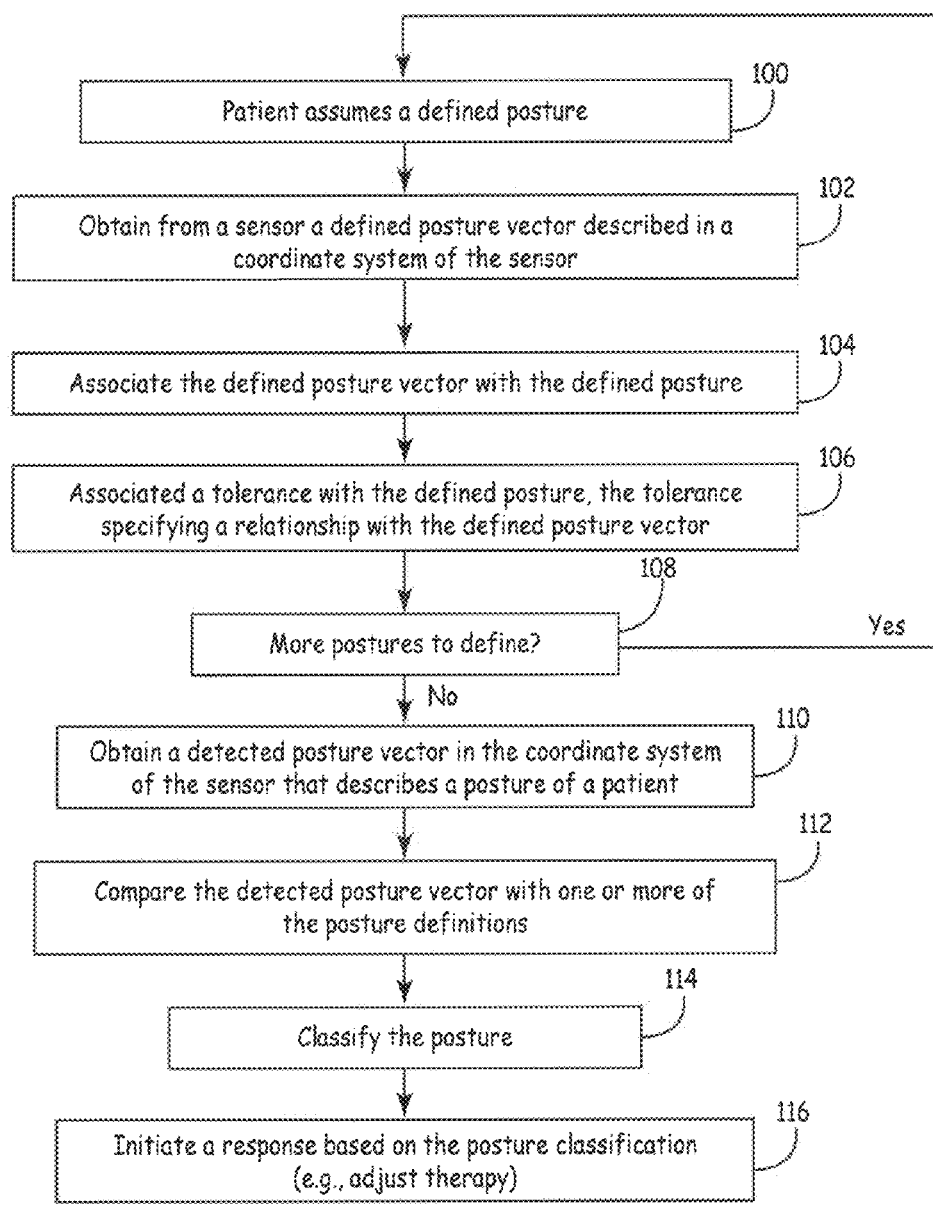
FIG. 6 is a flow diagram describing one method of creating and using posture definitions according to the current disclosure.

FIG. 6 is a flow diagram describing one method of defining posture definitions and using these definitions to classify a patient's posture according to one embodiment of the current disclosure. First, a patient is directed to assume a posture (100). This may be any posture whatsoever. While the patient assumes this posture, a defined posture vector is obtained from sensor 40 that is described in a coordinate system of the sensor (102). The defined posture vector is associated with a defined posture (104). This may be accomplished by storing an indication of the defined posture along with an indication of the defined posture vector, for example. A tolerance is also associated with the defined posture (106). This tolerance specifies a relationship with the defined posture vector. This relationship may describe one or more regions in space (e.g., cone, toroid, etc.) positioned relative to a defined posture vector. The regions may be described in multiple ways (e.g., using trigonometric functions, a straight-line distance, a city-block distance, an inner product, etc.). The relationship may further involve a minimum (e.g., "falls within"), a maximum (e.g., "falls outside of"), and/or Boolean logic. The association of the tolerance may be accomplished by storing the tolerance along with the indication of the defined posture. If any more postures are to be defined (108), the definition process is repeated by returning to step 100.

After one or more postures are defined in the foregoing manner, processing continues to step 110, where a detected posture vector describing a current posture of a patient is obtained. This detected posture vector is obtained from sensor 40 in the coordinate system of the sensor. The detected posture vector is compare with one or more of the posture definitions to determine whether this detected posture vector has a specified relationship with a defined posture vector as set forth by any of the posture definitions (112). The patient's posture is then classified based on this determination (114).

Some response or action may then be initiated based on the posture classification (116). This response is related to treatment of, and/or providing care to, the patient. Such care may involve automatically modifying a therapy that is currently being delivered, or selecting a new therapy for delivery to the patient. In another embodiment, the detected posture may be used to prompt some notification, or to initiate recording of some information.

The process of FIG. 6 may be repeated periodically, as at the sampling rate of sensor 40, at some other predetermined time period, upon the occurrence of some detected event, or based on some other occurrence within the system.

It is possible that the detected posture vector does not have a relationship with any of the defined posture vectors included in any of the posture definitions. In this case, the patient's posture may be classified as Undefined and the desired actions associated with the Undefined posture classification may be initiated. In another embodiment, when this occurs, the patient remains classified in the posture in which he was last classified. That is, the patient's most recent posture classification remains unchanged.

The above description focuses on mechanisms for defining and classifying a posture using a coordinate system of the sensor. In particular, this mechanism includes defining postures using the coordinate system of the sensor, obtaining a detected posture vector in the coordinate system of the system, and directly comparing the two vectors to classify the patient's posture. This mechanism may be applied to postures as well as to activity states that are described using vectors, as will be discussed below in reference to classification of activity states.

Next, more specific techniques for comparing detected posture vectors to defined posture vectors are discussed. One way to accomplish this involves comparing angles. For instance, the determination as to whether $V_{pt}$ 84 (FIG. 5B) lies within toroid 88 may be based on a comparison between $\theta_{Ld}$ 80, $\theta_{Ld\,2}$ 86 and $\beta_{Up}$ 89. Specifically, if $\theta_{Ld}$ 80<$\beta_{Up}$ 89<$\theta_{Ld\,2}$ 86, the patient may be classified in the Lying Down posture according to the definition illustrated in FIG. 5B. To perform this type of classification, however, the angle $\beta_{Up}$ 89 between $V_{pt}$ 84 and $V_{Up}$ must first be determined, a step that is highly processing intensive, and which requires a relatively large power expenditure. This is not advantageous, particularly when implantable devices are being used to perform the classification.

An alternative to the foregoing relates to referencing values referred to herein as similarity values (or simply "similarities"). A similarity is a metric that indicates how similar two vectors are to one another, but is not an angle, and does not require derivation of, or comparison between, angles. As an example, some type of scalar (non-angular) distance such as a maximum straight-line distance between vectors may be used as a similarity. Other examples include a "city-block" distance, a Euclidean distance, an absolute difference, a Minkowski (p-norm) distance, an inner product, or some other mathematical relationship that compares the two vectors. In one particular embodiment, a cosine or another trigonometric function (sine) is used as a similarity. When similarities rather than angles are used to perform posture classification, posture classification may be completed with relatively few processing steps. This saves a significant amount of power and allows processing to complete faster, as is illustrated in the remaining drawings.

Figure 7A:
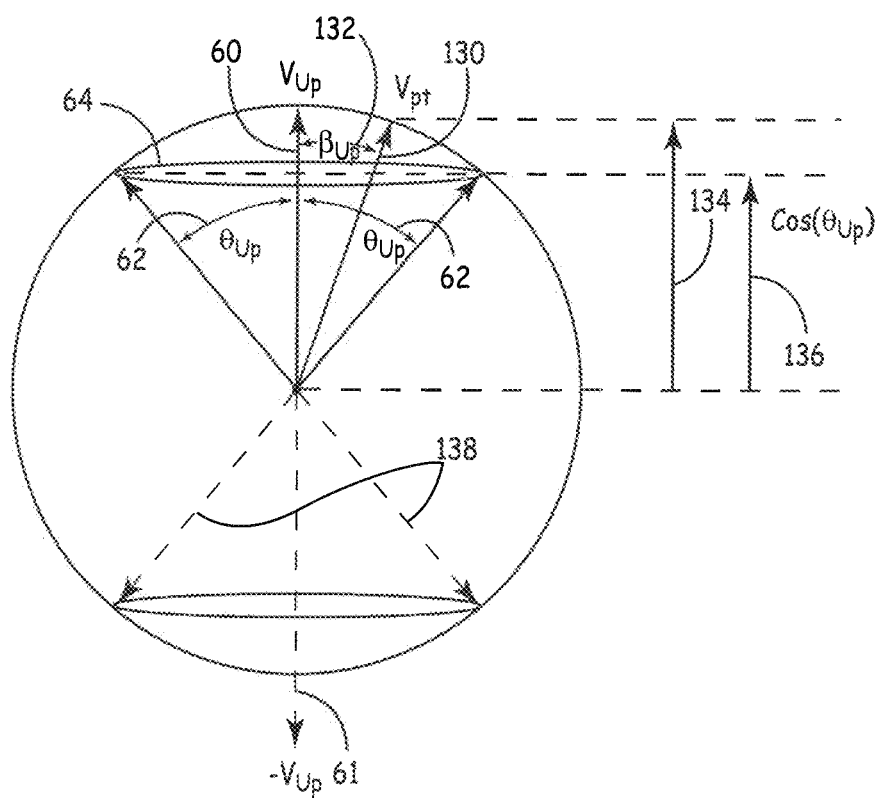
FIG. 7A is a graphical depiction of a posture definition for the Upright posture.

FIG. 7A is a graphical depiction of a posture definition for the Upright posture. This posture is defined in terms of vector $V_{Up}$ 60 and a tolerance that may reference angle $\theta_{Up}$ 62. As previously described in reference to FIGS. 5A and 5B, the angle $\theta_{Up}$ may be used to describe a cone 64 surrounding vector $V_{Up}$. In this example, a patient's posture will be classified as being Upright if the detected posture vector $V_{pt}$ 130 for the patient lies within cone 64.

One way to determine whether $V_{pt}$ 130 falls within cone 64 is to derive $\beta_{Up}$, which is the angle between $V_{pt}$ 130 and $V_{Up}$ 60. This angle $\beta_{Up}$ may then be compared to $\theta_{Up}$ 62 which defines the cone size. As previously discussed, this is processing intensive, and may therefore be considered undesirable.

As an alternative to determining the angle $\beta_{Up}$, a comparison between cosines for angles $\beta_{Up}$ and $\theta_{Up}$ may be used instead as follows:

$$\text{If } \cos(\beta_{Up}) \geq \cos(\theta_{Up}), \text{ Posture=Upright} \qquad \text{(Equation 1)}$$

This relationship is depicted by FIG. 7A, which shows the cosine of the angle $\beta_{Up}$ 132 via arrow 134. The cosine of the angle $\theta_{Up}$ is designated by arrow 136. In this case, cos ($\beta_{Up}$) is greater than cos ($\theta_{Up}$). Therefore, the patient will be classified as being in the Upright posture.

The cosine of angle $\beta_{Up}$ between detected posture vector $V_{pt}=[V_{pt1}\,V_{pt2}\,V_{pt3}]$ and defined posture vector $V_{Up}=[V_{Up1},V_{Up2},V_{Up3}]$ may be described as follows:

$$\cos(\beta_{Up}) = \frac{V_{pt1} \cdot V_{Up1} + V_{pt2} \cdot V_{Up2} + V_{pt3} \cdot V_{Up3}}{\sqrt{V_{Up1}^2 + V_{Up2}^2 + V_{Up3}^2} \cdot \sqrt{V_{pt1}^2 + V_{pt2}^2 + V_{pt3}^2}} \qquad \text{(Equation 2)}$$

By using a similar equation to express cos ($\theta_{Up}$), substituting cosine values into Equation 1, and squaring both sides of the resulting Equation (which is advantageous to eliminate processing-intensive square root operations), the following relationship is obtained:

$$(V_{pt1} \cdot V_{Up1} + V_{pt2} \cdot V_{Up2} + V_{pt3} \cdot V_{Up3})^2 \geq \cos^2(\theta_{Up}) \cdot (V_{Up1}^2 + V_{Up2}^2 + V_{Up3}^2) \cdot (V_{pt1}^2 + V_{pt2}^2 + V_{pt3}^2)$$ (Equation 3)

According to this relationship, the patient may be classified in an Upright posture so long as the relationship of Equation 3 is true, and the inner product of $(V_{pt1} \cdot V_{Up1} + V_{pt2} \cdot V_{Up2} + V_{pt3} \cdot V_{Up3})$ is greater than zero.

Equation 3 illustrates how similarity values (in this case cosines) may be used to evaluate the patient's posture without use of processing-intensive operations, such as those involving angle derivation and square root operations. Processing operations are further streamlined by recognizing that the terms $\cos^2(\theta_{Up}) \cdot (V_{Up1}^2 + V_{Up2}^2 + V_{Up3}^2)$ appearing in Equation 3 produce a constant value. The value for this constant may be calculated once for a given posture (in this case, the Upright posture), and thereafter may be used whenever a comparison with the Upright posture vector is performed, further simplifying processing steps.

FIG. 7A further includes a second cone 138 that may be described as a mirror image of cone 130. This second cone 138 surrounds a vector $-V_{Up}$ 61, which is 180 degrees from vector $V_{Up}$ 60. The cone may be used to define an Inverted posture, for instance. Relationships similar to those described above may be used to determine whether a detected posture vector falls within cone 138. This determination, like that shown above, may be completed without angle derivations according to the current methods.

Figure 7B:
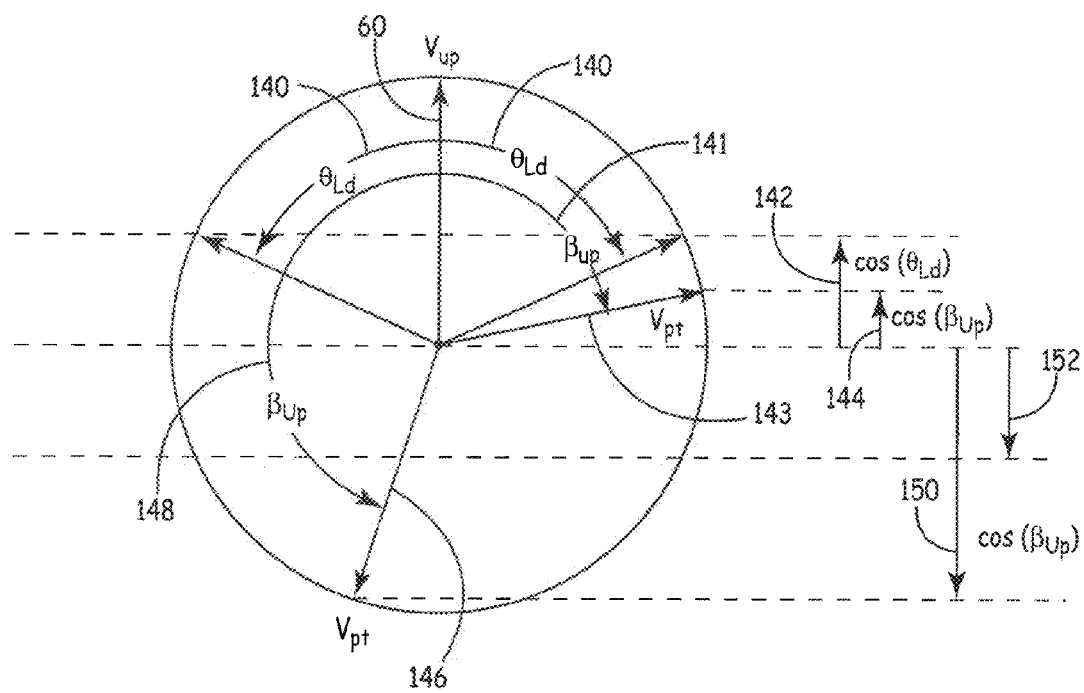
FIG. 7B is a graphical depiction of a posture definition for a Lying Down posture.

FIG. 7B is a graphical depiction of a posture definition for a Lying Down posture such as that already discussed in reference to FIG. 5B above. As previously described, the patient may be defined as being in the Lying Down posture whenever a detected posture vector $V_{pt}$ 143 is outside of the cone 64 that surrounds vector $V_{Up}$ 60. Using a cosine as a similarity value, this tolerance relationship may be expressed as follows:

If $\cos(\beta_{Up}) \leq \cos(\theta_{Ld})$, Posture=Lying Down (Equation 4)

Angle $\beta_{Up}$ is the angle between the detected posture vector $V_{Up}$ and the detected posture vector $V_{pt}$ 143.

In the current example, the foregoing relationship is satisfied. The cosine of the angle $\beta_{Up}$ is represented by arrow 144, and the cosine of angle $\theta_{Ld}$ 140 is represented by arrow 142. It may be seen that the cosine of the angle $\beta_{Up}$ 144 is less than the cosine of angle $\theta_{Ld}$ 142 such that a patient having the detected posture vector $V_{pt}$ 143 will be classified as being in the Lying Down posture.

Next, assume the detected posture vector shown as $V_{pt}$ 146 is obtained. Using the foregoing relationship of Equation 4, this detected posture vector will likewise be classified as Lying Down. This will be true even though posture vector $V_{pt}$ 146 may be more aptly categorized as being associated with an inverted position. This posture classification will occur because the cosine of angle $\beta_{Up}$ 148 between $V_{pt}$ 146 and $V_{Up}$ 60 (represented by arrow 150) is less than the cosine 142 of angle $\theta_{Ld}$. It may be desirable to exclude such posture vectors from a Lying Down definition. To accomplish this, the following tolerance relationship may instead be used to define the Lying Down posture:

If $|\cos(\beta_{Up})| \leq \cos(\theta_{Ld})$, Posture=Lying Down (Equation 5)

This excludes all vectors for which the cosine of the angle between the detected posture vector and $V_{Up}$ is less than negative of the cosine of angle $\theta_{Ld}$. Thus, the minimum allowable cosine that satisfies the relationship of Equation 3 is represented by arrow 152.

As was the case described above in regards to FIG. 7A, using similarities such as a cosine of an angle to define tolerances allows posture classification to be completed in a manner that eliminates the need to determine angles. This is highly advantageous in an application wherein it is desirable to conserve power, as is the case with IMD applications. These mechanisms may be applied to specific prone postures, such as is shown in reference to FIGS. 8A and 8B.

Figure 8A:
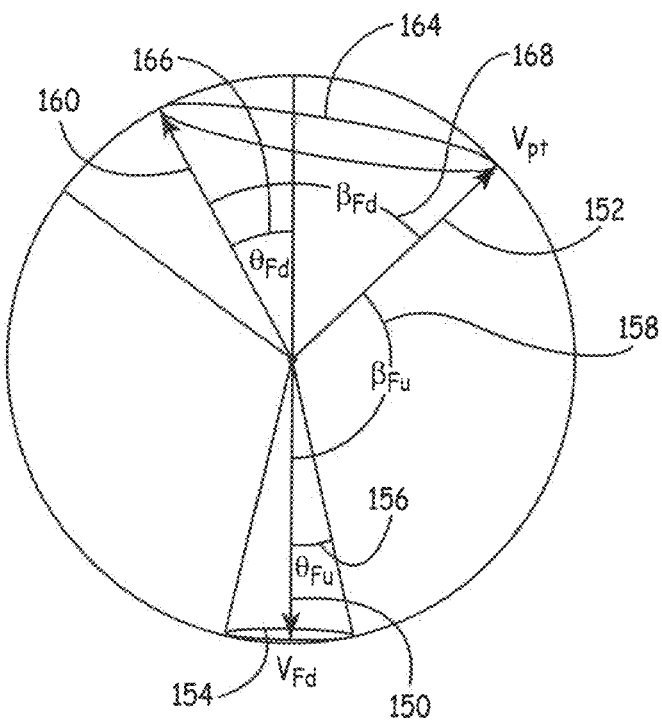
FIGS. 8A and 8B are graphical depictions of posture definitions for multiple postures that a patient may assume when lying down.
Figure 8B:
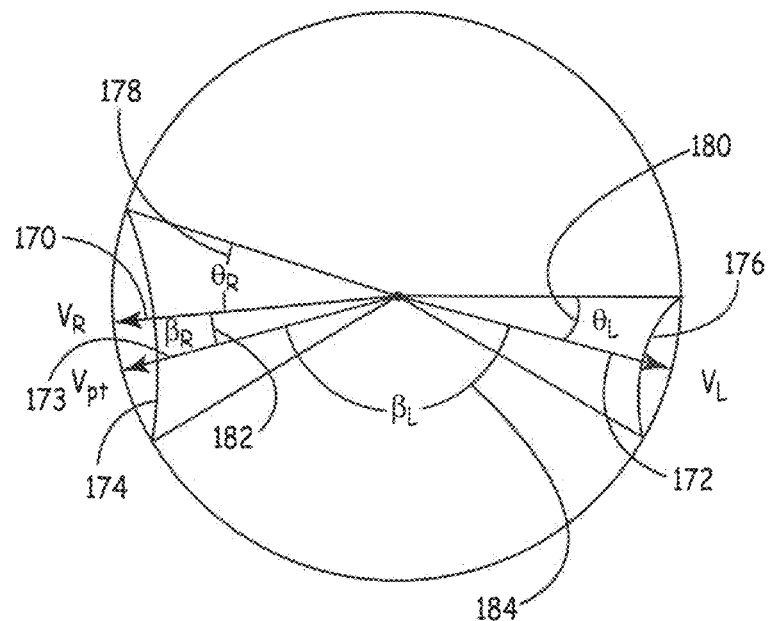

FIGS. 8A and 8B are graphical depictions of posture definitions for multiple postures that a patient may assume when lying down. In one embodiment, these graphs may occupy a plane in which the A-P 58c and L-M 58b axes of the patient resides (FIG. 4), but this need not be the case.

Postures occupied by a patient when lying down may include a Face Up posture when the patient is on his back, a Face Down posture assumed when the patient is lying on his stomach, a Right Side posture when the patient is on his right side, and a Left Side posture when the patient is on his left side. These vectors may, but need not be, co-planar. Moreover, the vectors need not be equidistant from one another, but may be anywhere within three-dimensional space.

In FIG. 8A, a defined posture vector $V_{Fd}$ 150 is used to define a Face Down posture. Detected posture vector $V_{pt}$ 152 will be associated with this Face Down posture if the detected posture vector $V_{pt}$ falls within a cone 154, wherein the size of the cone may be defined by the cosine of angle $\theta_{Fd}$ 156. One way to make this classification is to determine whether the cosine of the angle $\beta_{Fd}$ 158 between the detected posture vector $V_{pt}$ 152 and the defined posture vector $V_{Fd}$ 150 is greater than the cosine of angle $\theta_{Fd}$. If so, the detected posture vector is within cone 154, and the patient will be determined to be in the Face Down posture.

In a similar manner, a second defined posture vector $V_{Fu}$ 160 is used to define the Face Up posture. Note that this vector need not be "opposite" of the $V_{Fd}$ 150, and indeed, need not even be co-planar with the Face Down vector. Detected posture vector $V_{pt}$ 152 will be associated with this Face Up posture if the detected posture vector $V_{pt}$ 152 falls within a cone 164 surrounding vector $V_{Fu}$, wherein the size of the cone may be defined by the cosine of angle $\theta_{Fu}$ 166. This classification may be made by determining whether the cosine of the angle $\beta_{Fu}$ 168 between the detected posture vector $V_{pt}$ 152 and the defined posture vector $V_{Fu}$ 160 is greater than the cosine of angle $\theta_{Fu}$ 166.

In the example of FIG. 8A, the detected posture vector $V_{pt}$ 152 will not be classified in either the Face Up or Face Down posture, since this vector does not fall within either one of cones 154 or 164.

FIG. 8B is a graphical depiction similar to that of FIG. 8A, but instead relates to the Right Side and Left Side postures which are associated with the defined posture vectors $V_R$ 170 and $V_L$ 172, respectively. A patient will be classified as being in the Right Side posture if detected posture vector $V_{pt}$ 173 falls within cone 174. This occurs when the cosine of the angle $\beta_R$ 182 between the detected posture vector $V_{pt}$ 173 and the defined posture vector $V_R$ 170 is greater than the cosine of the angle $\theta_R$ 178. Conversely, the patient will be classified as being in the Left Side posture if the detected posture vector falls within cone 176. This occurs when the cosine of the angle $\beta_L$ 184 between the detected posture vector $V_{pt}$ 173 and the defined posture vector $V_L$ 172 is greater than the cosine of the angle $\theta_L$ 180.

In the foregoing manner, any number of N postures may be defined to classify a patient who is lying down. The four postures shown in FIGS. 8A and 8B are merely exemplary. These postures may, but need not be co-planar, and may be in any relationship to one another. The cones surrounding a particular vector need not be in any size relative to the other cones. This provides a very flexible approach to defined postures. Other mechanisms for classifying lying down postures are described in commonly-assigned patent application entitled "Posture State Classification for a Medical Device", referenced above.

As previously described, the cosine provides one example of a similarity value that may be used to classify a patient's posture without derivation of angles. Other similarities may be used in the alternative. For instance, a "smallest sine" relationship may be utilized rather than a "largest cosine" relationship to determine a closest defined posture vector to a detected posture vector. As another example, a city-block distance d (V, $V_{pt}$) may be derived between a detected posture vector $V_{pt}$=[$V_{pt1}$ $V_{pt2}$ $V_{pt3}$] and a defined posture vector V=[$V_1$ $V_2$ $V_3$] as follows:

$$d(V,V_{pt})=|V_1-V_{pt1}|+|V_2-V_{pt2}|+|V_3-V_{pt3}| \quad \text{(Equation 6)}$$

A variation of this technique provides a Euclidean distance as follows:

$$d(V,V_{pt})=\sqrt{(V_1-V_{pt1})^2+(V_2-V_{pt2})^2+(V_3-V_{pt3})^2} \quad \text{(Equation 7)}$$

Yet another technique utilizes a maximum absolute difference $d_\infty$(V, $V_{pt}$) as follows:

$$d_\infty(V,Vpt)=\max\{|V_1-V_{pt1}|,|V_2-V_{pt2}|,|V_3-V_{pt3}|\} \quad \text{(Equation 8)}$$

As another example, a Minkowski (P-Norm) distance may be used. Other mechanisms may be used to describe a similarity between two vectors that does not involve the calculation of an angle.

As may be appreciated, the types of distance relationships discussed above in reference to Equations 6-8, as well as certain trigonometric functions (e.g., sine of angles) generate similarity values having an inverse relationship to the degree of similarity existing between the two vectors that are being compared. For example, when any of the distances described by Equations 6-8 generate a value of "0", the two compared vectors are the same. That is, the vectors are perfectly similar. Conversely, the distance increases as the vectors become less similar.

In cases such as the foregoing, it may be desirable to use a mapping function that maps this original similarity value to a new value that will be directly proportional to the degree of similarity existing between the compared vectors. For instance, the mapping function may involve subtracting the original similarity value from some maximum value. As a specific example, the sine of an angle may be subtracted from "one" so that the new similarity value will be directly proportional to the degree of similarity between the compared vectors. To illustrate, this mapping function will convert a sine of "one" to a new similarity value of "zero", and so on. The mapping function may instead involve subtracting the similarity value from some other maximum possible similarity value.

Any of the types of similarity values described above, including cosines, sines, distances, and so on, may be used to define a posture in any of the ways described above. That is, a posture definition may be created that includes a defined posture vector and a tolerance. The tolerance describes a relationship that references one or more similarities of any of the types described herein. During use, a detected posture vector is obtained from a patient and compared to a defined posture vector to obtain a similarity that is preferably of the type referenced by the posture definitions so that a meaningful comparison may be performed. If this similarity fulfills the relationship specified by the tolerance, the patient is classified as being in the defined posture.

Next, posture definitions that reference multiple regions in space are considered. In all of the foregoing examples, a posture definition involves a single region in space. This single region is defined using a vector and a tolerance. For instance, a region in space may be a cone, a toroid, the space outside of a cone, or any other type of region in space that may be accurately described and referenced by a tolerance.

It is possible for two regions in space that are associated with two different posture definitions to overlap. For instance, FIG. 5B illustrates a toroid defined for the Lying Down posture. This toroid surrounds a mid-section of a patient. If the patient's detected posture vector falls anywhere within this toroid, the patient will be classified as Lying Down. This toroid likely overlaps cones defined in the manner shown in FIGS. 8A and 8B. Thus, a patient may be classified in the Lying Down posture at the same time the patient may also be classified in any of the Face Up, Face Down, Right Side, and Left Side postures. It may be desirable to merge such regions in space for inclusion in a single posture definition.

Figure 9A:
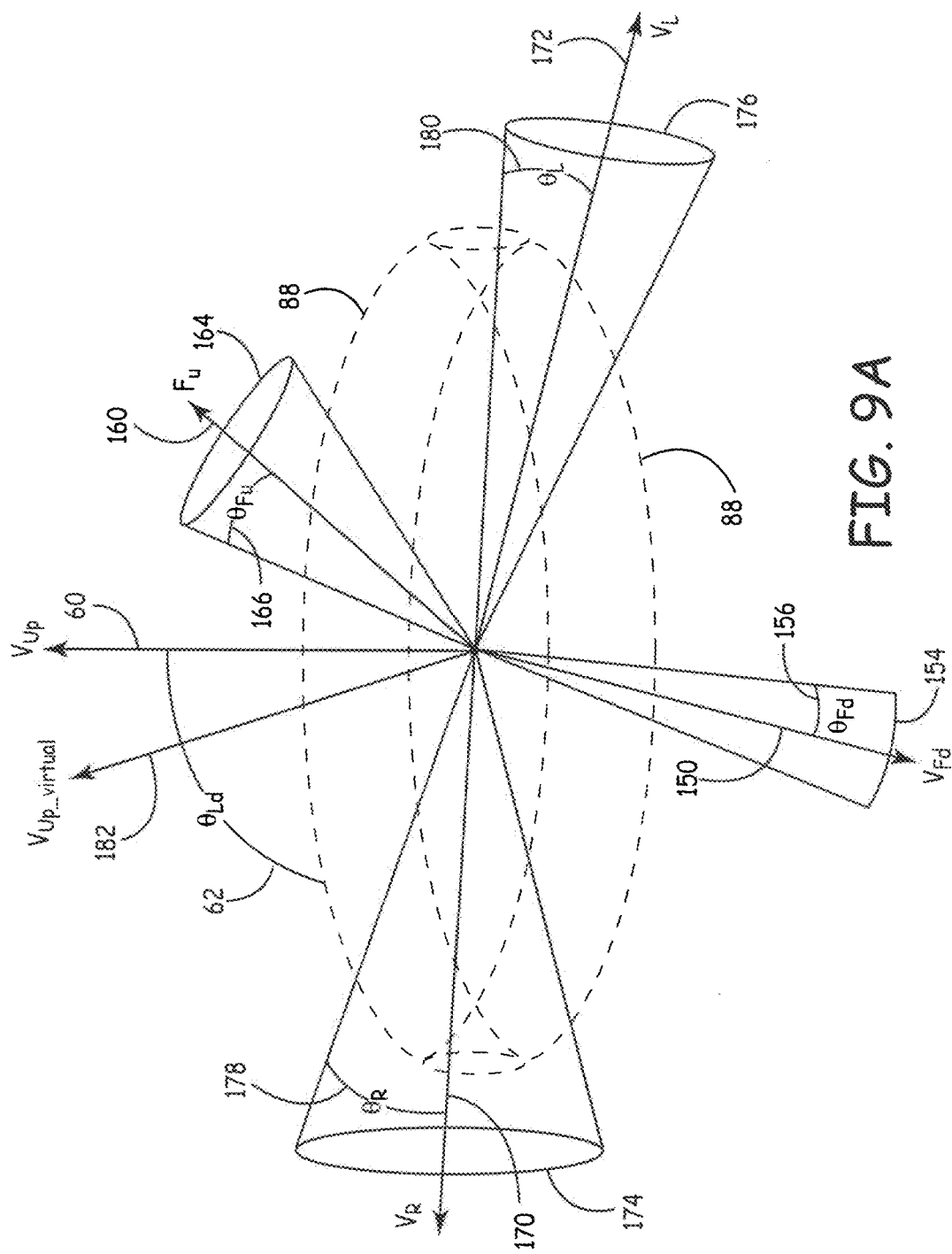
FIGS. 9A and 9B are graphical depictions of multiple regions in space being referenced by a single posture definition.

FIG. 9A is a graphical depiction of toroid 88 of FIG. 5B being overlaid with the four cones 154, 164, 174, and 176 of FIGS. 8A and 8B. For purposes of this description, it will be assumed that $\theta_{Ld}$ 80 and $\theta_{Ld2}$ 86 are selected such that the cosine of $\theta_{Ld}$ is equal to the negative cosine of $\theta_{Ld2}$ (that is, the toroid is symmetrical about an axis that is perpendicular to the Upright posture vector $V_{Up}$ 60). This is to simplify the current discussion. However, it will be understood that a posture definition may alternatively include an asymmetrical toroid.

The five regions in space may be combined to define a Lying Down posture as follows:

If $|\cos(\beta_{Up})|\leq\cos(\theta_{Ld})$ OR $\cos(\beta_{Fu})\geq\cos(\theta_{Fu})$ OR $\cos(\beta_{Fd})\geq\cos(\theta_{Fd})$ OR $\cos(\beta_R)\geq\cos(\theta_R)$ OR $\cos(\beta_L)\geq\cos(\theta_L)$ then Posture=Lying Down (Equation 9)

In this way, if the patient's detected posture vector falls within one or more of the regions in space defined by this equation, the patient will be classified in the Lying Down posture.

The type of definition described in reference to Equation 9 is useful in regards to defining the Lying Down posture, since a patient who is reclining may often lie with his head above his feet, particularly when in the Face Up posture. In such cases, the angle at which the patient is reclining may place the patient outside of the area included within toroid 88. If the toroid alone is being used to classify the patient's posture, a patient in the Face Up posture may not be classified as Lying Down. This situation may be addressed by overlaying a cone that is large enough to accurately classify the Face Up posture upon toroid 88, as described in reference to Equation 9. Using this type of definition for the Lying Down posture, the patient in the Face Up posture will be accurately classified as Lying Down.

While the various regions may overlap to be included within the same posture definition, this is not a requirement. For instance, a cone that does not overlap any portion of toroid 88 or any other cone in FIG. 5A may be included within the definition for the Lying Down posture, if desired.

The various techniques described in reference to FIG. 9A allow the system to benefit from use of both toroids and cones. In particular, the system provides the sensitivity obtained when using a toroid to detect the Lying Down posture. The system further incorporates the specificity of a cone-based approach that allows for independent adjustment of cone sizes. For instance, as discussed above, a cone associated with a Face Up posture may be selected to be relatively large to accommodate a patient who prefers to recline Face Up at an angle that is relatively large. If desired, the cone for the Face Down posture may be substantially smaller because the patient may lie with his/her head only slightly elevated while in this posture. Thus, use of toroids and cones provides a very high degree of flexibility when defining the Lying Down posture. Of course, such techniques may be applied to any other posture, and is not limited to use with the Lying Down posture.

As may be appreciated, by incorporating the toroid into the definition, the patient will remain classified in the Lying Down posture no matter how that patient rotates when in a prone position. For instance, the patient may be transitioning from a Face Up to a Left Side posture. During this transition, the detected posture vector may have exited the cone for the Face Up posture while not yet having entered the cone for the Left Side posture. Without use of the toroid, the patient may, in one embodiment, enter a region where his posture is Undefined. Because of use of the toroid, however, the patient will remain classified as being Lying Down. In one embodiment, this classification of Lying Down is used to provide hysteresis in the system such that the patient's previous prone posture sub-classification for the Lying Down posture (in this example, the Face Up posture sub-classification) is retained until the patient enters a new prone posture sub-classification (in this case, the Left Side posture sub-classification). Therefore, use of techniques such as described in reference to Equation 9 may result in more flexible and accurate posture classification.

The foregoing illustrates how Boolean Logic may be employed to combine various regions in space for posture classification purposes. As another example, two defined posture vectors, each being associated with respective tolerances, may describe two cones in three-dimensional space. A posture definition may specify that only the area within both of the two cones will be included in the defined posture. This is shown in reference to FIG. 9B.

Figure 9B:
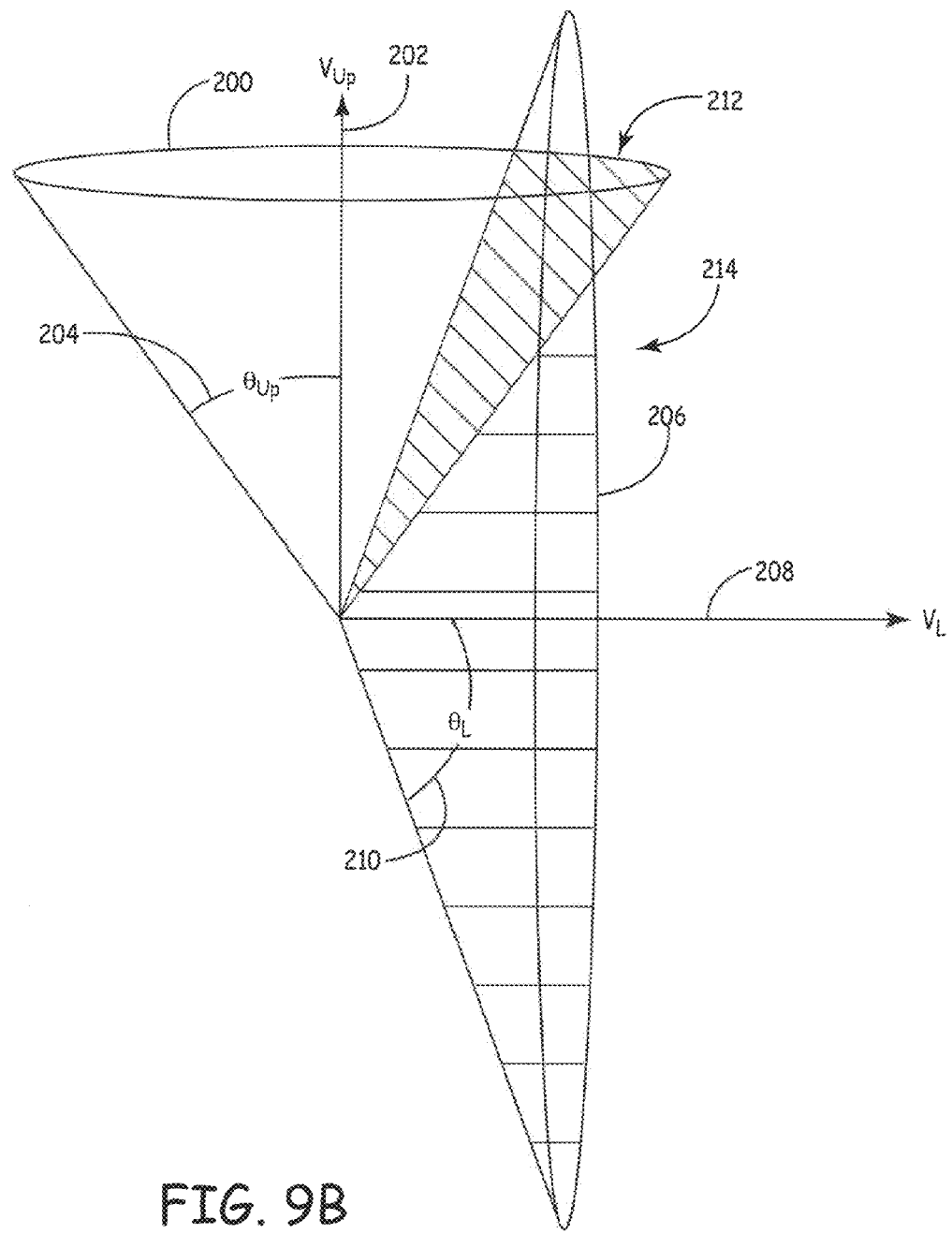

FIG. 9B is a graphical depiction of a first cone 200 surrounding a defined posture vector $V_{Up}$ 202 associated with an Upright posture The size of the cone is defined by the angle $\theta_{Up}$ 204. A detected posture vector will fall within cone 200 if the angle $\beta_{Up}$ between the detected posture vector and $V_{Up}$ satisfies the following relationship:

If $\cos(\beta_{Up}) \geq \cos(\theta_{Up})$ (Equation 10)

A second cone 206 surrounds a defined posture vector $V_L$ 208 associated with the patient lying on his left side. The size of this cone is defined by the angle $\theta_L$ 210. A detected posture vector will fall within cone 206 if the angle $\beta_L$ between the detected posture vector and $V_L$ satisfies the following relationship:

If $\cos(\beta_L) \geq \cos(\theta_L)$ (Equation 11)

An area that satisfies both relationships may be used to define an exemplary Leaning posture, as follows:

If $\cos(\beta_{Up}) \geq \cos(\theta_{Up})$ AND $\cos(\beta_L) \geq \cos(\theta_L)$ then Posture=Leaning (Equation 12)

The area satisfying this type of relationships will include the intersection of the two cones, shown as hashed area 212 in FIG. 9B.

Another type of relationship may include the following:

If $\cos(\beta_L) \geq \cos(\theta_L)$ AND NOT $\cos(\beta_{Up}) \geq \cos(\theta_{Up})$ then Posture=Left Side2 (Equation 13)

This alternative posture for the patient's Left Side includes the hashed region 214 portion of cone 206, but excludes hashed region 212. Thus, area included within one of two overlapping regions but not the other may be used to create a posture definition. These concepts may be expanded to include any number of regions in three-dimensional space that may be interrelated by any types of Boolean logical functions known in the art.

The discussion of FIGS. 9A and 9B provides alternative ways to reference one or more regions in space for inclusion with a single posture definition. Use of multiple spatial regions may involve Boolean Logic, for instance. Another way to achieve a similar result involves linking multiple posture definitions together. For instance, consider again the example of Equation 9 that allows five spatial regions (a toroid and four cones) to be referenced by a single posture definition. Instead of referencing these five regions in the same definition, each of the five regions could be referenced by a respective posture definition, and the five posture definitions could then be linked for response purposes. According to the latter approach, wherein the patient is detected as being in any one of the linked postures, the same response is taken (e.g., a same program group or a common set of therapy parameter values may be used to provide therapy). Merging or linking definitions in this manner may be useful for examples in which a same action or set of actions is to be initiated for all linked postures (e.g., a common set of therapy parameter values is to be used for providing therapy). Thus this alternative approach may utilize up to five posture definitions that are linked together to achieve similar results to that obtained using the five spatial regions that are linked according to Equation 9 above.

Next, alternatives are considered for obtaining the defined posture vectors that are used in posture definitions.

As discussed above, defined posture vectors may be obtained through patient participation. A patient is asked to assume a posture and a vector is obtained from signals provided by sensor 40. This is an "actual" defined posture vector because it corresponds to an actual posture assumed by the patient.

Another type of defined posture vector is "virtual" rather than "actual". A virtual defined posture vector (or simply "virtual posture vector") is a vector that may be obtained by applying processing steps to one or more of the other defined posture vectors. This can be appreciated by returning to FIG. 9A.

In FIG. 9A, each of the cones associated with a prone posture is defined using a corresponding defined posture vector $V_{Fu}$ 160, $V_{Fd}$ 150, $V_R$ 170, and $V_L$ 172. These four vectors may be used to obtain a virtual posture vector for the Upright posture. This virtual vector may, but need not, correspond to the actual defined posture vector $V_{Up}$ 60.

According to one method, a virtual posture vector for the Upright posture is obtained using multiple cross-products. For instance, a cross-product between the vectors for the Face Down and the Left Side postures (that is, $V_{Fd}$ cross $V_L$) may be used to derive a vector $V_{Norm1}$ that is perpendicular to both $V_{Fd}$ and $V_L$. Using the cross-product identity, $V_{Norm1}$ may be expressed as:

$$V_{Norm1} = \frac{V_{Fd} \times V_L}{\sqrt{V_{Fd1}^2 + V_{Fd2}^2 + V_{Fd3}^2} \cdot \sqrt{V_{L1}^2 + V_{L2}^2 + V_{L3}^2} \cdot \sin(\theta_{Fd\_L})}$$ (Equation 14)

where $\theta_{Fd\_L}$ is the angle between the defined posture vectors $V_{Fd}$ and $V_L$. In Equation 14, the numerator is a vector, as follows:

$$V_{Fd} \times V_L = V_{FdxL} = [V_{FdxL1}, V_{FdxL2}, V_{FdxL3}] \quad \text{(Equation 15)}$$

As discussed above, for purposes of this disclosure, the first, second, and third terms of the vector array in Equation 15 correspond to the x-, y-, and z-axis components of the vector The first, or x-axis component, may be determined as follows:

$$V_{FdxL1} = V_{Fu1} \cdot V_{L3} - V_{Fu3} \cdot V_{L1} \quad \text{(Equation 16)}$$

The second, or y-axis component, may be determined as follows:

$$V_{FdxL2} = V_{Fu2} \cdot V_{L3} - V_{Fu3} \cdot V_{L2} \quad \text{(Equation 17)}$$

The third, or z-axis component, may be determined as follows:

$$V_{FdxL3} = V_{Fu1} \cdot V_{L2} - V_{Fu2} \cdot V_{L1} \quad \text{(Equation 18)}$$

$V_{Norm1}$ will be a vector that will be perpendicular to the two crossed vectors and that has a direction determined by the right-hand rule. This direction may correspond somewhat to the S-I axis of the patient and will also be in the same general direction as the defined posture vector $V_{Up}$.

In a similar manner, three additional normal vectors $V_{Norm2}$, $V_{Norm3}$, and $V_{Norm4}$, may be determined for adjacent vector pairs $(V_L, V_{Fu})$, $(V_{Fu}, V_R)$, and $(V_R, V_{Fd})$, respectively, keeping in mind that the cross-product relationship is not commutative. In each case, the resulting vector $V_{Norm2}$, $V_{Norm3}$, and $V_{Norm4}$ is perpendicular to the two vectors used to produce the vector, and will have a direction determined by the right-hand rule. This direction may generally coincide with the S-I axis of the patient.

The four resulting vectors $V_{Norm1}$-$V_{Norm4}$ may then be averaged to obtain vector $V_{Up\_virtual}$ 182. As may be appreciated, in this example, averaging is accomplished by adding the first vector components of each of $V_{Norm1}$-$V_{Norm4}$ (that is, all four of the x-axis components) and dividing by four to obtain the first vector component of $V_{Up\_virtual}$. Similarly, all of the second vector components (that is, all four of the y-axis components) may be averaged to obtain the second vector component of $V_{Up\_virtual}$, and all of the third vector components may be averaged to obtain the third vector component of $V_{Up\_virtual}$.

The resulting virtual posture vector $V_{Up\_virtual}$ 182 may have a direction that is generally perpendicular to the average of the lying down postures, and which may correspond somewhat to the S-I axis of the patient. While the virtual vector will have a same general direction as the defined posture vector $V_{Up}$, the two vectors need not be the same.

The above described processing techniques may be applied to any number of N postures defined within the system, and is not limited to the four defined postures described above. In one embodiment, each normal vector $V_{Normx}$ is obtained as the cross-product of two adjacent vectors, taking into account that the cross-product is not commutative, and the right-hand rule must be followed. As one example, this may involve obtaining the cross-products while traveling in a counter-clockwise direction around the patient's S-I axis. As another example, this may involve traveling in a clockwise direction, and then using the negative of the average as the virtual posture vector.

In the above example, each of the defined posture vectors $V_{Fu}$, $V_L$, $V_{Fd}$, and $V_R$ used to generate the virtual vector is a defined posture vector obtained by having the patient assume the Face Up, Left Side, Face Down, and Right Side positions in the manner discussed above. However, the concept is not so limited. In another embodiment, a virtual vector may be obtained as an average of the cross-products of other defined vectors that are unrelated to postures the patient assumes while lying down. Moreover, a virtual vector may be obtained using other virtual vectors alone, or in combination with, defined posture vectors. Moreover, the cross-products need not be formed by crossing adjacent vector pairs, but could be obtained using non-adjacent vector pairs in another embodiment.

According to another approach for determining a virtual vector, a plane is located that best approximates the subspace of the vectors being used to obtain the virtual vector. For instance, in this example, a plane is located that best approximates the subspace of the four defined posture vectors $V_{Fu}$, $V_{Fd}$, $V_R$, and $V_L$. This can be done by calculating the two singular dominant vectors that best approximate these four lying down vectors, and then obtaining the cross-product of the two dominant vectors. To accomplish this, a three-by-four matrix $X = [V_{Fu}, V_{Fd}, V_R, V_L]$ is formed that contains each of the defined posture vectors for the four lying down postures. A singular value decomposition may then be used to find the two orthogonal vectors that best approximates the range of X. The singular value decomposition S has the following relationship to X:

$$X = USV^T \quad \text{(Equation 19)}$$

wherein U is an orthogonal matrix of left singular vectors, S is a matrix of singular values, V is an orthogonal matrix of right singular vectors, and T represents the transpose operation.

According to this method, the two vectors from the left singular matrix U with the largest singular values are selected. These two vectors form the best approximating plane of the three-dimensional space spanned by the four vectors in matrix X. That is, the function provides a determination of the two-rank (planar) approximation of X. The two selected vectors may be referred to as $U_1$ and $U_2$. The virtual vector may then be obtained as the cross-product of $U_1$ and $U_2$.

When using the foregoing approach, it is important to ensure that the appropriate ordering of vectors is used to obtain a cross-product having the same general direction as the defined posture vector $V_{Up}$. This could be ascertained, for instance, by determining whether the inner product between the resulting virtual vector and vector $V_{Up}$ is positive. If this is not the case, the resulting virtual vector and vector $V_{Up}$ are not in a same general direction.

If $V_{Up}$ is not in the same general direction as the obtained virtual vector, the ordering of the vectors $U_1$, $U_2$ that was used to obtain the virtual vector is reversed and the cross-product is determined to obtain a virtual vector that is in the same general direction as $V_{Up}$.

Still other types of functions may be utilized to derive other types of virtual vectors. In some embodiments, for instance, the virtual posture vector may be obtained by taking a negative of the average of cross-products. Alternatively, the processing need not take into account averages of multiple cross-products, but may instead be a virtual vector obtained using one cross-product. In yet another example, the virtual vector may be obtained as an average of multiple vectors without using cross-products at all. Statistical techniques other than averaging may be employed to obtain the virtual posture vector. Thus, many types and combinations of processing steps may be contemplated to generate virtual posture vectors from multiple defined posture vectors for use in defining postures. Moreover, virtual posture vectors may be used alone, or in combination with, defined posture vectors to derive other virtual posture vectors. Use of virtual posture vectors to create posture definitions is discussed in reference to FIGS. 10A and 10B.

Figure 10A:
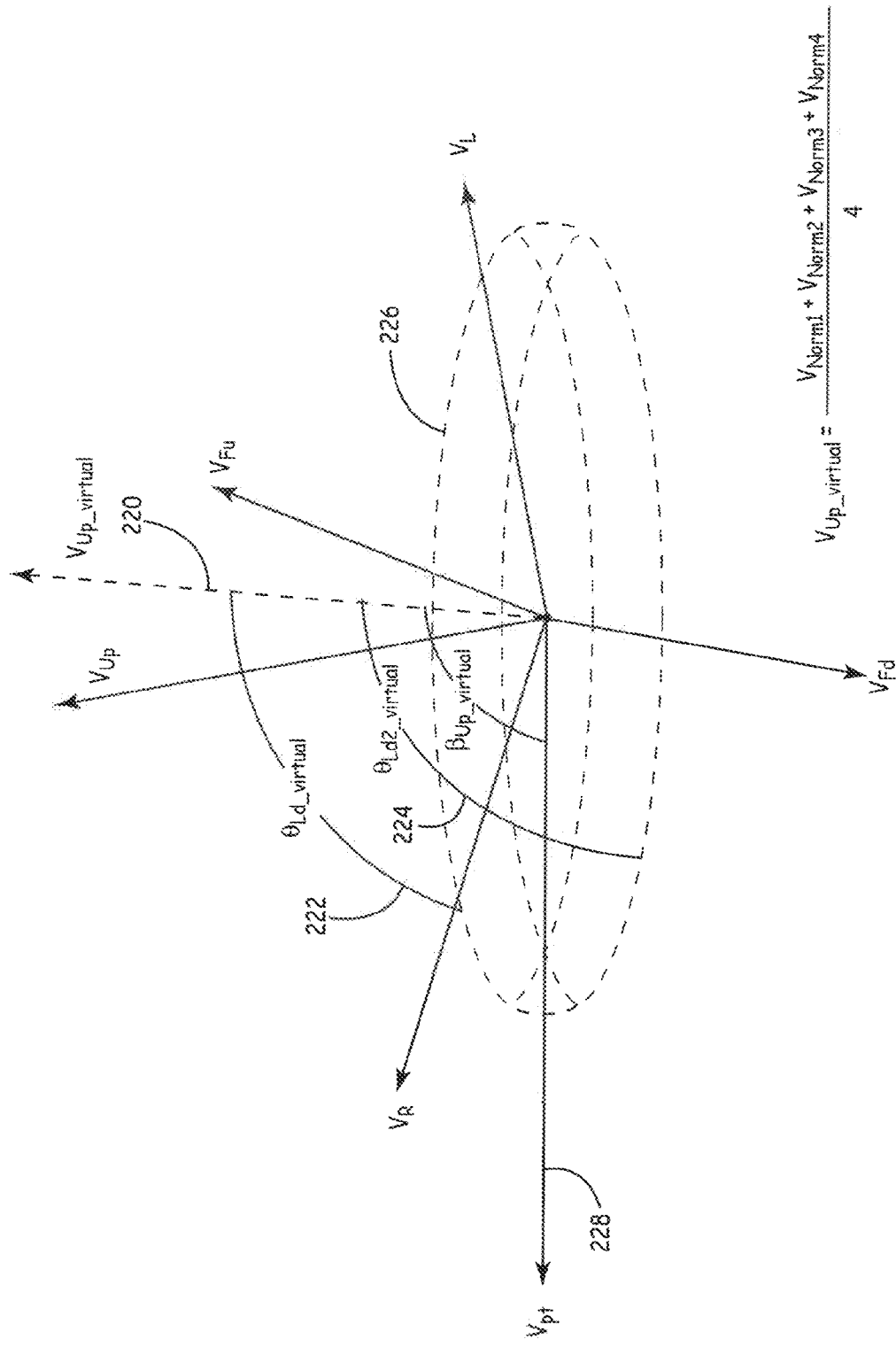
FIG. 10A is a graphical depiction of a posture definition that utilizes a virtual posture vector.

FIG. 10A is a graphical representation of a posture definition that utilizes the virtual posture vector $V_{Up\_virtual}$ 220 (shown dashed), which is a vector derived from the average of cross-products of adjacent pairs of the prone postures in the manner described above. This virtual posture vector may be used to define a posture that is similar to that shown in FIG. 5B. As in FIG. 5B, two angles $\theta_{Ld\_virtual}$ 222 and $\theta_{Ld2\_virtual}$ 224 may be provided in reference to the virtual posture vector $V_{Up\_virtual}$. These two angles may be used to describe a toroid 226 around the virtual posture vector 220. A posture definition for a Lying Down posture may reference these angles as follows:

If $\cos(\theta_{Ld2\_virtual}) \leq \cos(\beta_{Up\_virtual}) \leq \cos(\theta_{Ld\_virtual})$,
posture=Lying Down     (Equation 20)

In this equation, angle $\beta_{Up\_virtual}$ is the angle between the detected posture vector $V_{pt}$ 228 and the virtual posture vector $V_{Up\_virtual}$ 220. By selecting $\theta_{Ld}$ 222 and $\theta_{Ld2}$ 224 such that $\cos(\theta_{Ld})$ is equal to the negative $\cos(\theta_{Ld2})$, this relationship may be simplified, if desired, as follows:

If $|\cos(\beta_{Up\_virtual})| \leq \cos(\theta_{Ld\_virtual})$, Posture=Lying Down     (Equation 21)

Defining the Lying Down posture using $V_{Up\_virtual}$ provides certain advantages. For instance, many patients may prefer to lie with their head "propped up" in some manner, as on pillows. To accurately include this type of posture within a toroid defined in terms of an actual defined posture vector $V_{Up}$ 60 (FIG. 9A), the angle $\theta_{Ld}$ 62 associated with $V_{Up}$ may have to be decreased. Otherwise, the patient's Face Up position may be inaccurately detected as being either in the Upright posture, or in an Undefined posture that is between the Upright posture and the Lying Down posture. However, decreasing the angle $\theta_{Ld}$ 62 in this manner may make detection of the Upright posture less sensitive, and could lead to false detection of the Lying Down posture in some situations.

The foregoing challenges may be addressed by using the virtual detected posture vector $V_{Up\_virtual}$ rather than the actual defined posture vector $V_{Up}$ for detection of the Lying Down posture. Because the virtual vector $V_{Up\_virtual}$ is closer to being normal to the various prone postures (e.g., Face Up, Face Down, etc.) than is the actual defined posture vector $V_{Up}$, the angle $\theta_{Ld\_virtual}$ may be selected so that when the patient is lying in a face up position with an elevated head, the patient will be classified as occupying the Lying Down posture. This results in more accurate posture detection of the Lying Down postures. Thus, in one embodiment, virtual posture vector $V_{Up\_virtual}$ may be used to detect the Lying Down posture, and the actual defined posture vector $V_{Up}$ may be used to detect the Upright posture, or other postures associated with the Upright posture (e.g., Upright and Leaning, for example).

Figure 10B:
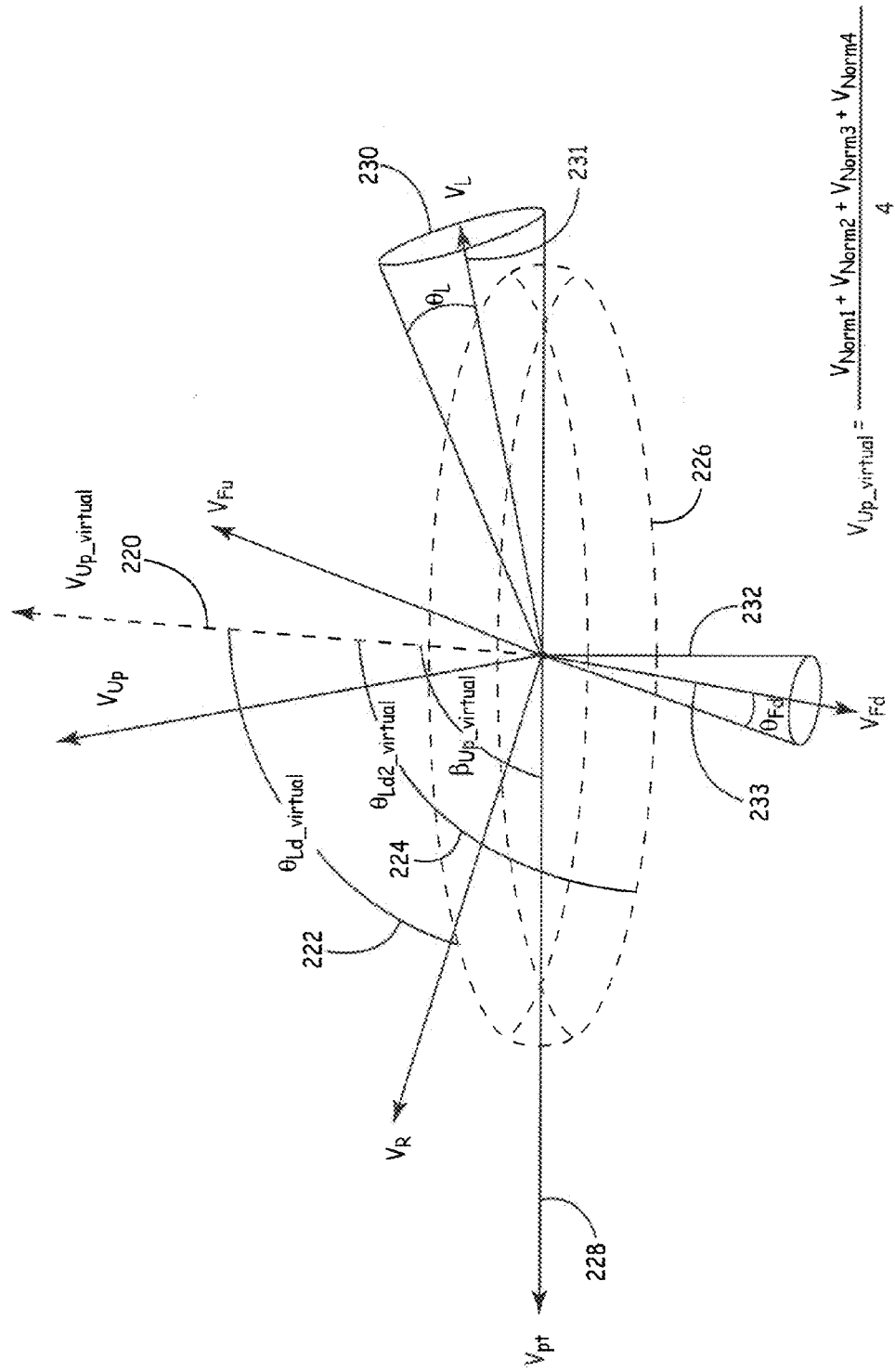
FIG. 10B is a graphical depiction of a posture definition that utilizes a virtual posture vector and references multiple regions in space.

FIG. 10B is a graphical representation of a posture definition that utilizes the virtual posture vector $V_{Up\_virtual}$ 220 in the manner shown in FIG. 10A, and that further overlays cones associated with prone posture vectors over the toroid 226. In this embodiment, only two cones are overlaid, a first cone 230 associated with the defined posture vector $V_L$ for the posture Left Side, and a second cone 232 associated with defined posture vector $V_{Fd}$ for the Face Down posture. Additional cones (e.g., Right Side, Face Up, etc.) may be included in a manner similar to that shown in FIG. 9A. The posture of FIG. 10B may have a definition as follows:

If $|\cos(\beta_{Up\_virtual})| \leq \cos(\theta_{Ld\_virtual})$ OR $\cos(\beta_{Fd}) \geq \cos(\theta_{Fd})$ OR $\cos(\beta_L) \geq \cos(\theta_L)$ then Posture=Lying Down     (Equation 22)

As in the examples above, $\beta_{Up\_virtual}$, $\beta_{Fd}$ and $\beta_L$ are angles between the detected posture vector $V_{pt}$ 228 and each of the virtual posture vector $V_{Up\_virtual}$ 220, $V_{Fd}$ 233, and $V_L$ 231 respectively.

The various techniques described in reference to FIG. 10B provide many benefits. For instance, as discussed above in reference to FIG. 9A, using both toroids and cones allows the system to incorporate the benefits of both approaches into the system. In particular, the system provides the sensitivity obtained when using a toroid to detect the Lying Down posture, while retaining the specificity and flexibility of a cone-based approach. Moreover, as discussed above, the use of the toroid allows hysteresis to be employed as the patient moves from one prone position (e.g., Face Up) to another posture (e.g., Left Side).

The approach of FIG. 10B further benefits from the use of the virtual vector $V_{Up\_virtual}$. This virtual vector is, in one embodiment, selected to be substantially normal to the plane that best approximates the planes that contain the defined posture vectors for the prone postures. Thus, the area within toroid 226 encompasses the area most likely to be occupied by the patient when the patient is in a prone posture. This is not necessarily true when the toroid is defined to surround $V_{Up}$. Therefore, many benefits are provided by embodiments that incorporate virtual vectors, a toroid, and one or more cones, in the manner shown in FIG. 10B.

As was the case above, virtual posture vectors may be included in any of the types of definitions involving any types of Boolean Logic functions. Regions defined using virtual vectors and regions defined using actual defined posture vectors may be referenced in the same definitions. Such regions may, but need not, overlap. This is described further in reference to the method of FIG. 11.

Figure 11:
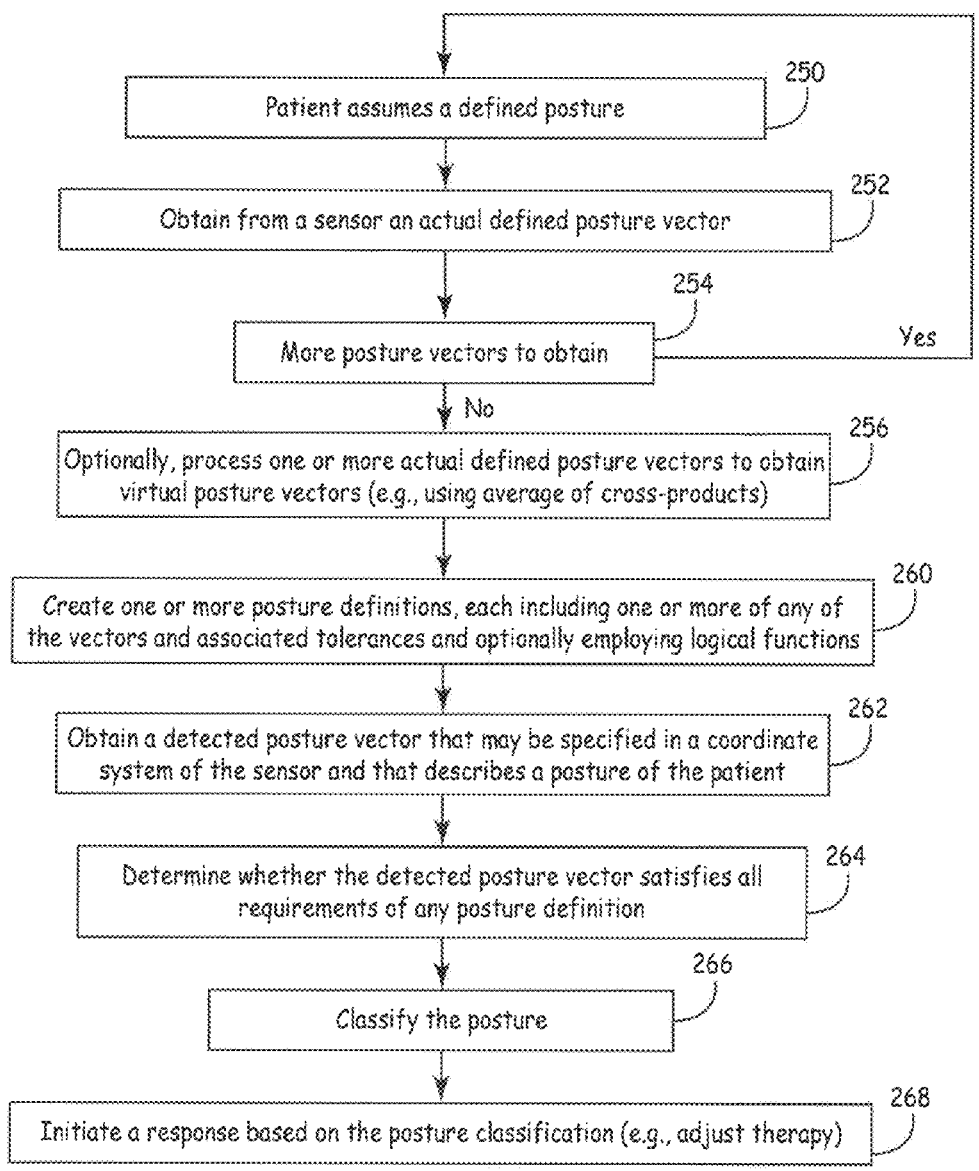
FIG. 11 is a flow diagram of a method of creating and using posture definitions according to one aspect of the disclosure.

FIG. 11 is a flow diagram of a method of creating and using posture definitions according to one aspect of the disclosure. A patient may be asked to assume a defined posture, such as the Upright posture (250). While the patient is in this posture, an actual defined posture vector is obtained from sensor 40 (252). If more defined posture vectors are to be obtained (254), the process returns to step 250. Otherwise, execution continues to step 256, where optional processing may be performed to obtain one or more virtual posture vectors from the actual defined posture vectors. Such processing may involve obtaining a virtual Upright vector from the average of the cross-products of adjacent pairs of the defined posture vectors for postures associated with lying down, for instance. Other types of processing may be performed in other embodiments to obtain different types of virtual vectors (e.g., averages, negative averages, negative averages of cross-products, etc.).

After one or more virtual posture vectors have optionally been obtained (256), posture definitions may be created that include one or more of the defined posture vectors and/or one or more of the virtual posture vectors and associated tolerances (260). Recall that these tolerances indicate a relationship between a respective defined posture vector and/or a virtual posture vector. These tolerances may reference a similarity, such as a cosine of an angle, rather than an angle itself, as may be desirable to obtain processing efficiencies in the manner discussed above discussed above. Moreover, multiple vectors and associated tolerances may be incorporated into a single definition by employing logical functions (e.g., AND, OR, NOT, etc.) such as exemplified above. Each such posture definition may be stored, if desired, as one of posture state definitions 52.

Next, a detected posture vector may be obtained from the sensor that describes the patient's posture (262). This detected posture vector is, in one embodiment, specified in the coordinate system of the system without regards to the coordinate system of the patient for ease of processing. This detected posture vector may be compared directly to the posture definitions to determine whether the detected posture vector satisfies all of the requirements of any of the posture definition (264). The patient's posture may be classified based on the results of the comparison (266). If the patient's posture does meet the requirements of a posture definition, the patient may be classified as occupying the associated posture. If, however, the patient's posture does not meet the requirements of any posture definition, the patient may be classified as being in an Undefined posture.

Some response or action may then be initiated based on the posture classification (268). This may involve automatically modifying a therapy that is currently being delivered, or selecting a new therapy for delivery to the patient. In another embodiment, the detected posture may be used to prompt some notification, or to initiate recording of some information.

The process of FIG. 11 may be repeated periodically, as at the sampling rate of sensor 40, at some other predetermined time period, upon the occurrence of some detected event, or based on some other occurrence within the system.

Figure 12:
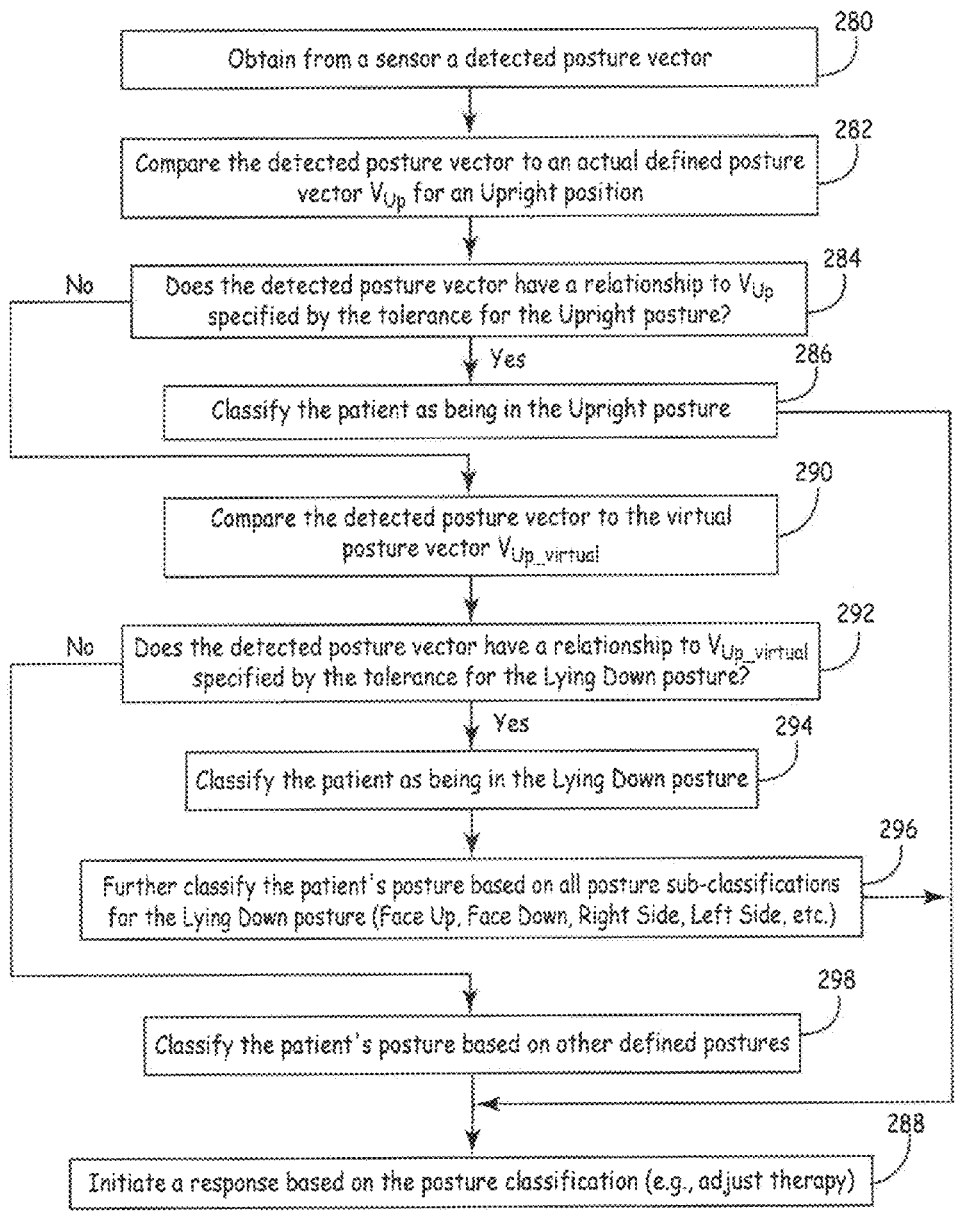
FIG. 12 is a flow diagram of a method of using posture definitions according to a more specific embodiment of the disclosure.

FIG. 12 is a flow diagram of a method of using posture definitions according to a more specific embodiment of the disclosure. A detected posture vector is obtained from sensor 40 (280). This detected posture vector is compared to an actual defined posture vector $V_{Up}$ for the Upright posture, wherein $V_{Up}$ may have been obtained as the patient occupied the Upright posture state (282). In another embodiment, this vector may have been selected by a clinician who provides the vector in the coordinate system of the sensor.

If the detected posture vector has a relationship to $V_{Up}$ specified by the tolerance for the Upright posture (284), the patient is classified as being in the Upright posture (286). Some response or action may then be initiated based on the posture classification (288). This may involve automatically modifying a therapy that is currently being delivered, or selecting a new therapy for delivery to the patient. In another embodiment, the detected posture may be used to prompt some notification, or to initiate recording of some information.

Returning to step 284, if the comparison of step 282 indicates that the detected posture vector does not have a relationship to the Upright posture as specified by the tolerance for that definition, execution continues to step 290, where the detected posture vector is compared to a virtual posture vector $V_{Up\_virtual}$ to determine whether the detected posture vector has a relationship to this virtual vector as specified by the tolerance for the Lying Down posture (292). If so, the patient is classified as being in the Lying Down posture (294). This classification for the Lying Down posture may involve use of any type of one or more regions in three-dimensional space. For instance, one or more toroids and/or one or more cones may be used for this purpose. Boolean Logic may be used to interrelate multiple spatial regions, if desired.

Next, if desired, the patient's Lying Down posture classification may be further refined by comparing the detected posture vector to all of the definitions for all "sub-classifications" of the Lying Down posture. Such sub-classifications may include the Face Up, Face Down, Right Side, and Left Side postures (296). Any number of such definitions may exist within the system for use in this manner. This may involve comparing the detected posture vector to cones surrounding each of the defined posture vectors for these postures, for example. Processing then continues to step 288 where some action may be taken based on the posture classification.

Returning to step 292, if the detected posture vector is not classified as being associated with the Lying Down posture, processing continues to step 298, wherein the detected posture vector may be compared to other defined posture vectors for other defined postures. This may include those postures other than the Upright posture and the Lying Down postures. Execution may then continue to step where some action is taken in response to the posture classification (288).

The process of FIG. 12 may be repeated periodically, as at the sampling rate of sensor 40, at some other predetermined time period, upon the occurrence of some detected event, or based on some other occurrence within the system.

Next, yet another method of evaluating a tolerance relationship is considered. In all of the foregoing examples, posture classification is described as involving determining whether a detected posture vector falls within some defined region in three-dimensional space, where the spatial region is specified by a tolerance of a posture definition. In an alternative embodiment, posture classification may simply involve determining to which defined posture vector the detected posture vector is closest. For instance, assume that a patient has been classified as being in the Lying Down posture. It may be desirable to further determine to which sub-classification of the Lying Down posture the patient's posture is closest, wherein such sub-classifications may include the Face Up, Face Down, Right Side, and Left Side postures. This type of processing may be applied in step 296 of FIG. 12, for example.

One way to determine which defined posture vector is closest to the detected posture vector involves considering the cosines of angles between the detected posture vector and each defined posture vector. Whichever angle has the largest cosine may be determined to be the closest defined posture vector. Alternatively, a "smallest sine" determination may be used instead of a "greatest cosine" determination.

According to one method, the foregoing determination may be simplified by normalizing all of the defined posture vectors in use within the system. To normalize a defined posture vector such as $V_{Up}=[V_{Up1}, V_{Up2}, V_{Up3}]$, each of the x, y, and z components of this vector are divided by the length $\|V_{Up}\|$ of the vector and multiplied by a scale factor S, as follows:

$$\text{Norm}(V_{Up}) = \frac{\lfloor V_{Up1}, V_{Up2}, V_{Up3} \rfloor}{\|V_{Up}\|} \times S \qquad \text{(Equation 23)}$$

$$\text{where } \|V_{Up}\| = \sqrt{V_{Up1}^2 + V_{Up2}^2 + V_{Up3}^2}$$

In this equation, "S" may be any selected value such as 1, 10, or 100. The same scale factor must be used when normalizing all of the vectors. When such normalization is performed, all defined posture vectors have the same length. As a result of this, the largest cosine determination is reduced to a determination involving inner products. That is, the closest defined posture vector to the detected posture vector will be the defined posture vector that produces the largest positive inner product with the detected posture vector.

As discussed above, the "closest to" relationship may be used to classify a patient's posture. This was as described above, wherein it is determined to which of the defined posture vectors of Face Up, Face Down, Right Side, Left Side the detected posture vector is closest and making a posture classification based on this finding. A more general use of this relationship will compare the detected posture vector to all defined posture vectors (rather than just those associated with prone postures) and then classify the patient's posture based on which defined posture vector is closest.

It may be noted that this type of "closest to" relationship is not limited to use of actual defined posture vectors, but may be generalized to include virtual posture vectors as well. Additional uses of this "closest to" relationship are described below.

The above description provides various types of processing techniques that may be used to streamline posture classification and/or make posture classification more flexible and robust. Yet another type of technique used for this purpose involves evaluating a condition referenced by a posture definition. This may be described by returning to the example of FIG. 7A. In that illustration, the Upright posture is defined in terms of the detected posture vector $V_{Up}$ 60 and a cone 64 surrounding $V_{Up}$ 60. According to that definition, so long as a detected posture vector $V_{pt}$ 130 is anywhere within the cone 64, the posture is classified as Upright. To be classified in association with Upright posture, it does not matter where within the cone 64 that $V_{pt}$ lies, only that $V_{pt}$ is somewhere within this cone.

In some circumstances, it may be advantageous to allow an aspect of the posture definition to be selectable based on evaluation of a condition. For instance, it may be desirable to allow the size of the cone surrounding $V_{Up}$ to be determined based on which side of the defined posture vector $V_{pt}$ lies. Specifically, when a patient is leaning backward, as may occur when the patient is in a reclining chair, it may be advantageous to detect that the patient has exited the Upright posture when the detected posture vector $V_{pt}$ is still relatively close to $V_{Up}$. This would allow a change in therapy to be triggered relatively quickly when the patient leans backwards into a reclining position, thus preventing patient discomfort that may occur if therapy levels associated with the Upright posture are utilized while the patient is leaning backward, as in a reclining chair.

Such considerations are not present when a patient is leaning forward. In fact, it may be desirable to allow the patient to continue to be classified in an Upright position even when the patient is in forward-leaning posture that is relatively far away from the $V_{Up}$ vector. This would allow the patient to continue receiving therapy associated with the Upright posture during such activities as stair climbing that may require the patient to lean forward in a substantial manner. During such activities, it is likely desirable to allow the same therapy associated with the Upright posture to be delivered to the patient.

In accordance with the foregoing example, the size of a cone surrounding $V_{Up}$ may be made selectable based on a condition. In this case, the condition involves determining whether a patient's detected posture vector $V_{pt}$ is closer to a Face Up posture vector $V_{Fu}$ such that the patient is backward leaning, or whether $V_{pt}$ is closer to a Face Down posture vector $V_{Fd}$ such that the patient is more forward leaning. If $V_{pt}$ is determined to be closer to the Face Up posture, a tolerance is selected that causes the patient to exit out of the Upright posture faster than if $V_{pt}$ is closer to the Face Down position. This may be appreciated further by considering FIG. 13.

Figure 13:
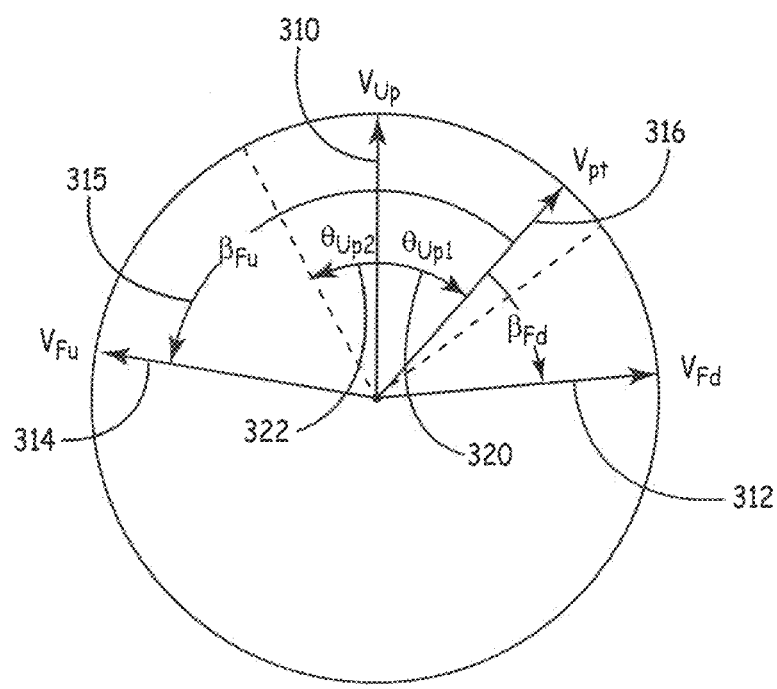
FIG. 13 is a graphical representation illustrating evaluation of a condition for selecting an aspect of the posture definition.

FIG. 13 is a graphical representation illustrating evaluation of a condition for selecting an aspect of the posture definition. In this example, vector $V_{Up}$ 310 is a defined posture vector used to define the Upright posture. This vector $V_{Up}$ may be an actual defined posture vector or a virtual posture vector according to any of the techniques described above. Defined posture vector $V_{Fd}$ 312 is associated with the Face Down posture, and defined posture vector $V_{Fu}$ 314 is associated with the Face Up posture.

A detected posture vector $V_{pt}$ 316 is obtained that describes the patient's current posture. According to the current aspect, this detected posture vector is compared to each of vectors $V_{Fd}$ 312 and $V_{Fu}$ 314 to determine to which of these defined posture vectors the detected posture vector is closest. This comparison may involve comparing angles (although this is not preferred in a power-limited embodiment), cosines or sines of angles, or some other similarity value (e.g., city-block, absolute different, Euclidean, etc.). As described above, according to one simple approach, inner products between $V_{pt}=[V_{pt1}, V_{pt2}, V_{pt3}]$ and each of the vectors $V_{Fu}$ or $V_{Fd}$ are derived. For instance, the inner product between $V_{pt}$ and $V_{Fu}=[V_{Fu1}, V_{Fu2}, V_{Fu3}]$ is as follows:

$$(V_{pt1} \cdot V_{Fu1} + V_{Fu2} \cdot V_{Up2} + V_{Fu3} \cdot V_{Up3}) \quad \text{(Equation 24)}$$

The one of the defined posture vectors resulting in the positive inner product may be determined to be closest to the detected posture vector.

In the example of FIG. 13, $V_{pt}$ 316 will have a positive inner product with $V_{Fd}$ 312 and a negative inner product with $V_{Fu}$ 314, wherein the negative inner product with $V_{Fu}$ is a result of the angle $\beta_{Fu}$ 315 between the defined posture vector $V_{Fu}$ and $V_{pt}$ being larger than 90 degrees. The outcome of this evaluation therefore selects $V_{Fd}$ as being "closest to" $V_{pt}$. The result of this outcome will be used to select some aspect of the posture definition. In the current example, this aspect is the angle to be used to define the cone surrounding $V_{Up}$. In particular, it will be assumed that angle $\theta_{Up1}$ 320 has been associated with $V_{Fd}$, and is therefore selected for use in defining the size of the cone. If the result of the evaluation had instead chosen $V_{Fu}$ 316 as the defined posture vector closest to $V_{pt}$, angle $\theta_{Up2}$ would have been selected for use with the Upright posture definition instead.

As may be appreciated, the selected angle $\theta_{Up1}$ 320 is larger than the angle $\theta_{Up2}$ 322 associated with $V_{Fu}$. When using this larger cone, $V_{pt}$ 316 falls within the cone, as shown in FIG. 13. The patient is therefore classified as being in the Upright posture, and will continue to receive therapy accordingly. This may correspond to a scenario, for instance, wherein the patient is leaning forward while climbing stairs, and would most benefit from receiving therapy associated with the Upright posture.

Next, assume that $V_{pt}$ 316 had been closer to $V_{Fu}$ 314 instead of $V_{Fd}$, but is still a same distance from $V_{Up}$ as is depicted in FIG. 13. In this case, angle $\theta_{Up2}$ 322 is selected for evaluating the Upright posture rather than angle $\theta_{Up1}$ 320. Because angle $\theta_{Up2}$ 322 is smaller than angle $\theta_{Up1}$ 320, $V_{pt}$ is no longer within tolerance for the Upright posture, even though $V_{pt}$ is no farther from $V_{Up}$ than it is in the scenario depicted in FIG. 13. As a result, the patient will be classified as having exited the Upright posture in this case.

This corresponds to the scenario wherein the patient is leaning backwards in a rocking chair with weight pressing against the spine. In this case, it may be desirable to exit the Upright posture state at least momentarily to allow therapy to be delivered according to some other posture, such as a Face Up posture. Otherwise, discomfort may occur if the patient continues to receive therapy associated with the Upright posture while leaning backwards, placing weight against the spine, for instance.

In the foregoing manner, some aspect of a posture definition may be made selectable based on evaluation of a condition. In this case, the condition involved two actual defined posture vectors $V_{Fu}$ and $V_{Fd}$. In other cases, more than two vectors may be involved in the comparison, and the vectors may be virtual and/or defined posture vectors. If desired, $V_{pt}$ 316 may be compared again N posture vectors (e.g., defined posture vectors for the Right Side, Left Side, Face Up, Face Down, etc.), with the result of all N comparisons being used to determine the tolerance. Moreover, the evaluation need not be limited to a two-way outcome. For instance, in this example involving N posture vectors, N or more outcomes may be possible from which to select (e.g., N different cone sizes).

In another embodiment, the condition being evaluated may involve some other type of comparison, such as a comparison involving a system parameter or physiological condition of the patient, rather than defined or virtual posture vectors.

While the exemplary evaluation involved a "closest to" determination for identifying to which of two vectors $V_{pt}$ was closest, this need not be the case. Any other type of relationship may be used when making this determination. For instance, a determination involving which vector is farthest, or which vector falls within some distance range, may be used in the alternative. The relationship may involve some other type of comparison rather than a comparison between two vectors, such as a comparison involving a system parameter or physiological condition of the patient.

Whereas the foregoing example involves selection of a cone size, this need not be the case. In another scenario, a selection of regions may be involved. For instance, a toroid-shaped region in space may be selected for use with a definition based on one outcome, and one or more cones may be selected for use with the definition based on another outcome. The size of these regions, the number of regions, the manner in which the regions are interrelated (e.g., using Boolean logic) may be selected based on evaluation of the condition.

Figure 14:
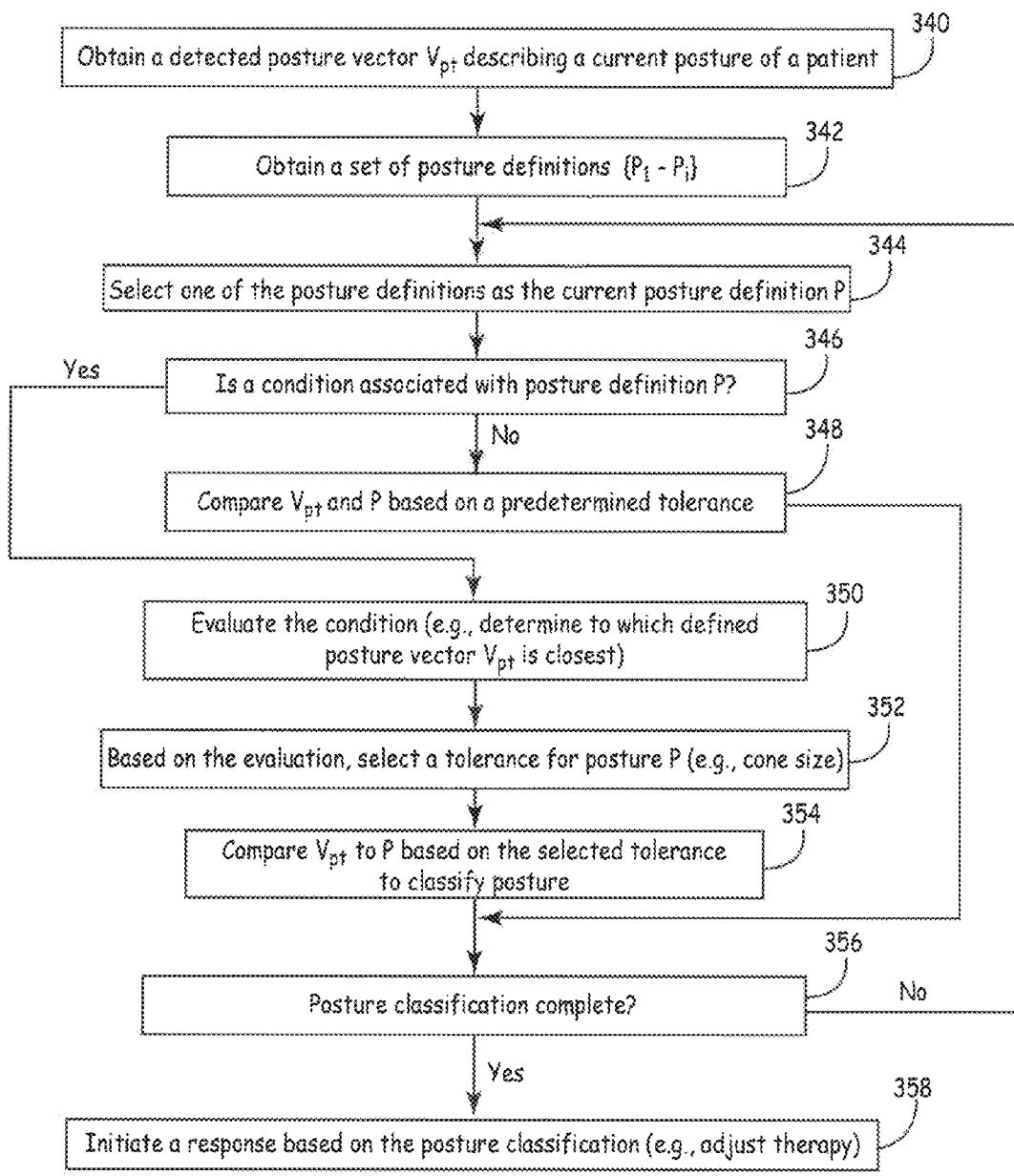
FIG. 14 is a flow diagram illustrating use of evaluated conditions when classifying postures.

FIG. 14 is a flow diagram illustrating use of evaluated conditions when classifying postures. First, a detected posture vector $V_{pt}$ is obtained for a patient's current posture (340). A set of posture definitions $\{P_1-P_i\}$ is obtained for use in posture classification (342). One of the posture definitions is selected for comparison to $V_{pt}$ (344). For instance, this may involve selecting a definition for the Lying Down posture for comparison to $V_{pt}$.

Next, it is determined whether a condition is associated with this posture definition (346). If not, the tolerance for this posture definition is compared to $V_{pt}$ to determine whether the patient should be classified as being in this posture (348). Processing continues to step 356, where it is determined whether posture classification is complete (356). Processing may be considered complete if the patient has been classified in the selected posture P (e.g., the Lying Down posture) and no further classifications are to occur (that is, this embodiment does not require any further classification of the patient's posture, such as into further sub-classifications of the Lying Down posture). If posture classification is not considered complete (e.g., either the patient's posture has not yet been classified, or the classification requires further classified), processing may return to step 344 for further classification or sub-classification of the patient's posture.

If posture classification is complete (356), some response may then be initiated based on the posture classification (358). This may involve automatically modifying a therapy that is currently being delivered, or selecting a new therapy for delivery to the patient. In another embodiment, the detected posture may be used to prompt some notification, initiate recording of some information, or performing some other response.

Returning to step 346, if it is determined that a condition is associated with the defined posture P, processing continues to step 350. There, the condition is evaluated. This may involve, for instance, determining to which defined posture vector in a set associated with the condition $V_{pt}$ is closest. This evaluation may be used to select a tolerance for posture P, which may involve selecting a cone size, for instance (352). The detected posture vector $V_{pt}$ may then be compared to the defined posture P base on the selected tolerance to determine whether the patient should be classified in this posture (354). If posture classification is considered complete (356), a response may be initiated based on the posture classification (358). Otherwise, processing returns to step 344 where another defined posture is selected and the process is repeated.

The process of FIG. 14 may be repeated periodically, as at the sampling rate of sensor 40, at some other predetermined time period, upon the occurrence of some detected event, or based on some other occurrence within the system.

The above discussion focuses on posture classification, which in one embodiment involves use of DC components of the x, y, and z signals of sensor 40. Similar techniques may be applied to classifying the motion of the patient. A patient's motion may be classified using activity states. In one embodiment, an activity state may be determined from the AC components of the outputs of sensor 40 (as opposed to DC components of the sensor output used to detect posture). For instance, outputs of sensor 40 may be filtered to retain a predetermined frequency range and exclude noise, processed according to various smoothing techniques, and then used to determine motion of a patient. Techniques for processing AC components of sensor 40 to obtain signals indicative of an activity state are described in provisionally-filed patent application entitled "Posture State Detection System and Method" and in commonly-assigned patent application entitled "Posture State Detection Using Selectable System Control Parameters" filed on even date herewith and referenced above.

A patient's motion may be classified using activity state definitions. An activity state definition may include a defined activity vector which is similar to a defined posture vector of a posture definition. This vector may relate to direction of velocity, direction of acceleration, or some other direction involving motion.

As was the case with posture definitions, an activity state definition may specify a tolerance describing a relationship to the defined activity vector. The tolerances may be expressed using relationships similar to those discussed above in regards to those used for posture definitions.

Activity state definitions may be created by a user such as a clinician. For instance, a clinician may prompt a patient to begin an activity such as walking on a treadmill. While this is occurring, a clinician may utilize clinician programmer 20 to transmit a command to IMD 12 to cause one or more vectors indicative of direction of motion of the patient to be obtained from outputs of sensor 40. If desired, the one or more vectors may be processed (e.g., to extract a certain frequency range, filter noise, and/or determine a median or average vector value for instance). The resulting vector may be used with a selected tolerance to define an activity state definition. In this manner, an activity state definition may reference a vector and a tolerance in much the same manner as a posture definition references a defined posture vector and a tolerance.

Once an activity state definition is created, it may be used to classify a patient's activity state. As the patient goes about daily life, the outputs of sensor 40 may be processed to derive a detected activity vector. This vector may be compared to the defined activity vectors contained within the activity state definitions. As was the case with comparison of posture vectors, this comparison may utilize similarities, which may be any of the types of similarities described above. The comparison may be accomplished using any of the techniques described above with respect to the comparison of defined posture vectors and detected posture vectors. In one embodiment, these techniques do not utilize angle derivations. Therefore, processing may be performed more efficiently. If the comparison indicates the detected activity parameter satisfies the requirements of a defined activity state, the patient may be classified as being in this activity state.

Therefore, it will be appreciated that all of the techniques described above in reference to posture definitions and posture vectors are applicable to vectors involved in activity state definitions. As previously described, this may involve obtaining the activity vectors in the coordinate system of the sensor 40 without reference to the patient's coordinate system. This may further involve utilizing non-angular similarities (e.g., trigonometric functions, inner products, distances, etc.) to make comparisons between a detected activity vector and an activity state definition. Activity definitions may involve conditions that must be evaluated before a tolerance may be selected. The definitions may involve multiple regions in space interrelated by Boolean logic functions. Alternatively, or additionally, the virtual activity vectors may be referenced in the activity state definitions. Thus, any of the techniques described herein are equally applicable to activity vectors as well as posture vectors.

As discussed previously, posture definitions and activity state definitions are each one subset of a more general class of definitions referred to as posture state definitions. A posture state definition references at least one of a defined posture and a defined activity state. Thus, a posture state may involve just a posture definition, just an activity state definition, or both.

Posture state definitions may be used to classify a patient's posture state. Such definitions may make use of any of the mechanisms herein described. Thus, a posture state definition may reference a posture and an activity state. The posture may be defined according to a defined posture vector and an associated tolerance. The activity state may be defined according to a defined activity vector and an associated tolerance. Any of the techniques described herein may be applied to either or both of the posture and the activity state referenced by the posture state definition.

Figure 15:
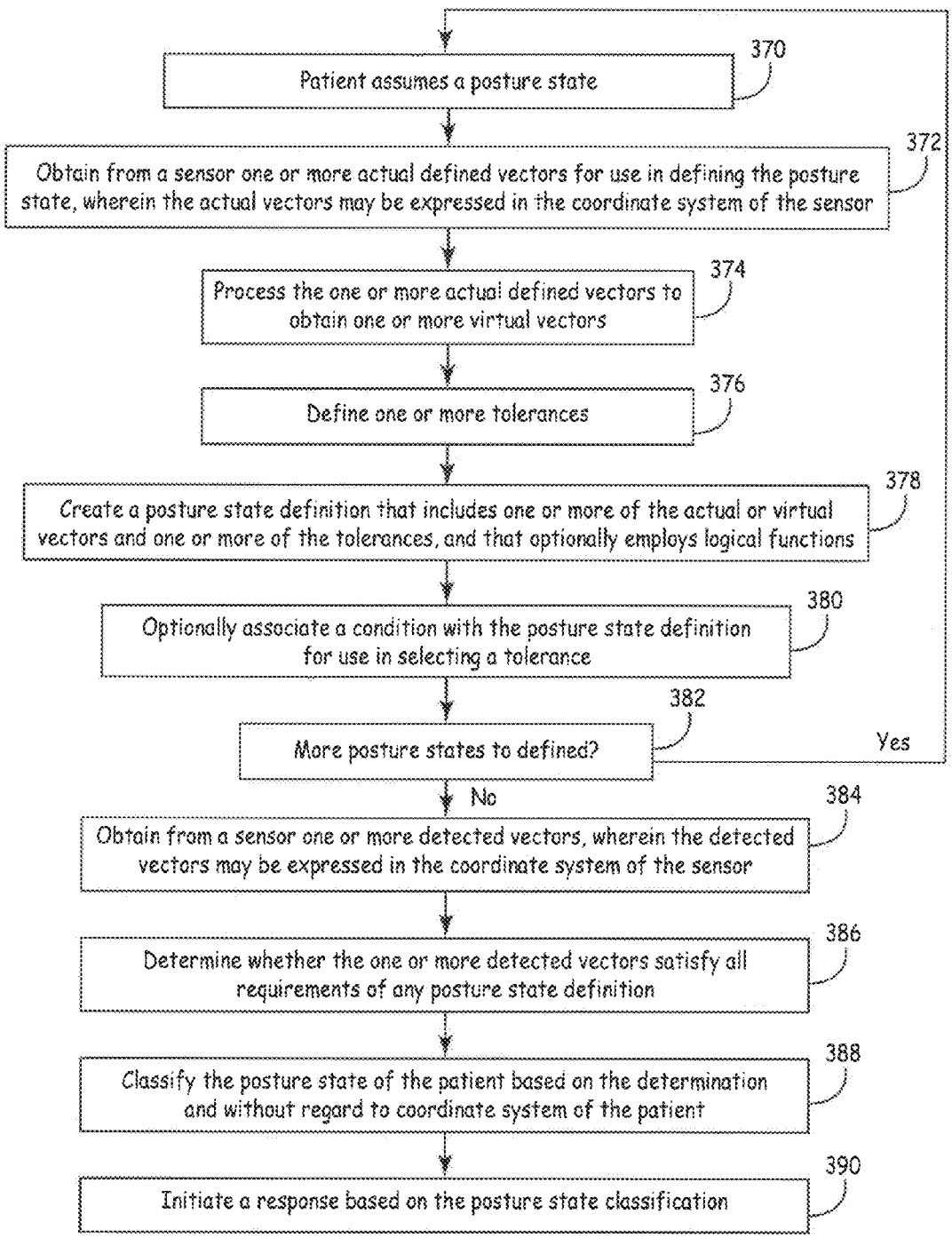
FIG. 15 is a flow diagram of one method of classifying a posture state according to the current disclosure.

FIG. 15 is a flow diagram of one method of classifying a posture state according to the current disclosure. The patient assumes a posture state, which involves at least one of posture and activity state (370). A sensor may be used to obtain one or more actual defined vectors for use in defining the posture state (372). The vectors that are obtained in this manner may be expressed in the coordinate system of the sensor to allow for more efficient processing.

The one or more actual defined vectors may be processed to obtain one or more virtual vectors (374). This processing may involve taking an average of multiple cross-products of vectors obtained in step 372, for instance. One or more tolerances may be defined (376). Each such tolerance may define a relationship to one of the actual vectors and/or the virtual vectors.

A posture state definition may be created that includes one or more of the actual and/or virtual vectors (378). The definition may further include one or more of the tolerances and may optionally employ logical functions (e.g., Boolean AND-, OR-, NOT-type functions, etc.). Optionally, a condition may be associated with the posture state definition for use in selecting a tolerance (380). For instance, this condition may compare the detected vector to one or more of the actual or virtual vectors to determine which is closest.

If more posture state definitions are to be created (382), processing may return to step 370. Otherwise, processing continues to step 384 where one or more detected vectors may be obtained. The detected vectors, which may be expressed in the coordinate system of the sensor, describes a posture state of the patient. It is determined whether the detected vectors satisfy all requirements of any posture state definition (386). This step may, in one embodiment, be performed using similarities that do not involve angle derivations. Moreover, this step may be performed solely using the coordinate system of the sensor, without reference to the patient's coordinate system. The posture state of the patient may be classified based on the comparisons of step 386 (388). According to one embodiment, this classification is performed without regard to the coordinate system of the patient.

Some response may then be initiated based on the posture classification (390). This may involve automatically modifying a therapy that is currently being delivered, or selecting a new therapy for delivery to the patient. In another embodiment, the detected posture may be used to prompt some notification, or to initiate recording of some information.

Next, an exemplary use interface is provided for orientating the sensor so that defined vectors and detected vectors are obtained in a coordinate system of sensor 40 and without regard to a coordinate system of the patient. This exemplary user interface is considered in regards to the remaining drawings.

Figure 16A:
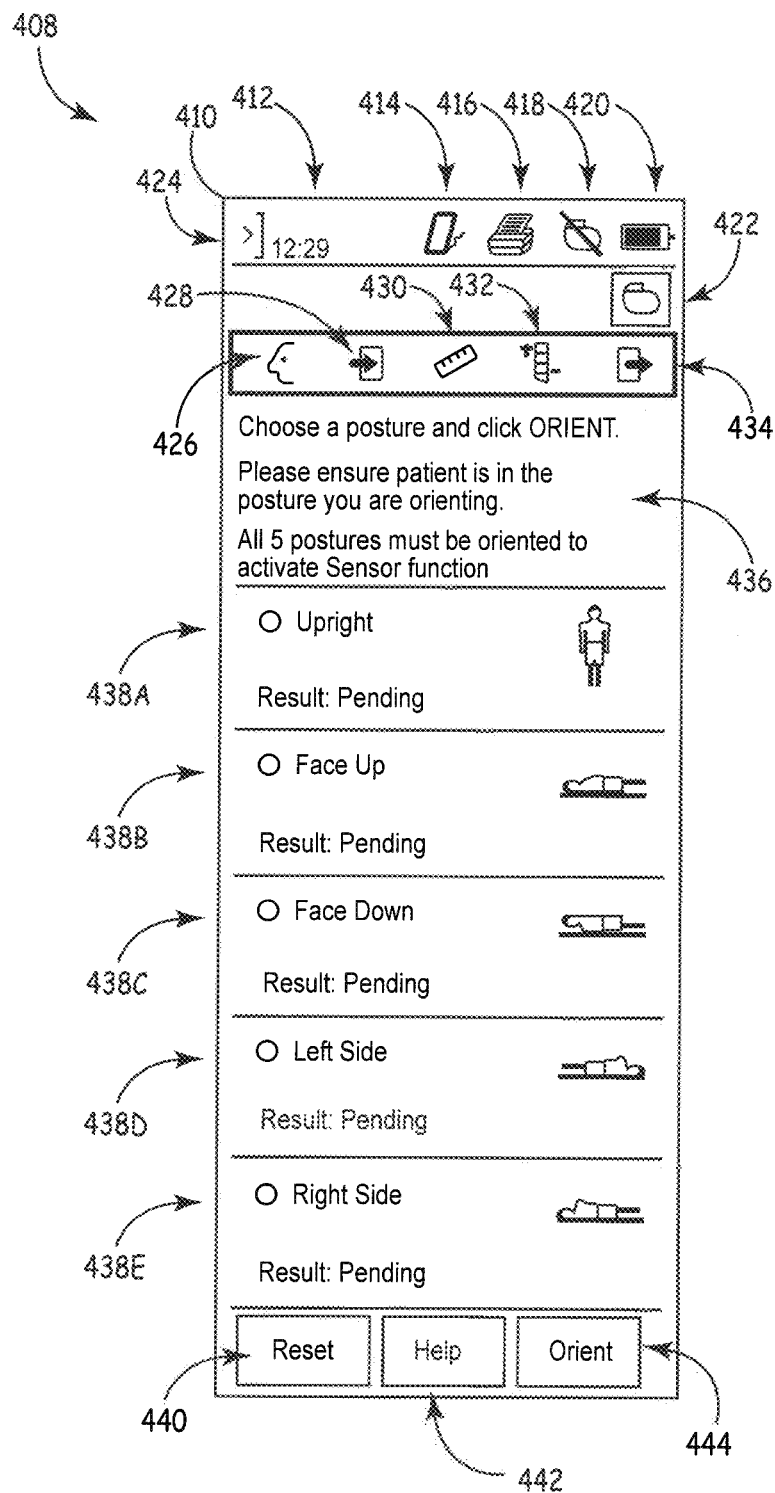
FIGS. 16A and 16B are conceptual diagrams illustrating an example user interface for orienting an implantable medical device with patient posture states prior to diagnostic or therapy use of the implantable medical device.

FIG. 16A is a conceptual diagram illustrating an example user interface 408 for orienting the implantable medical device prior to diagnostic or therapy use. User interface 408 is described as generally being displayed by a programmer 20, which may be a clinician programmer, a patient programmer or some other external programmer or remote device. User interface 408 displays information related to sensing posture states, automatic posture response, reviewing recorded therapy adjustment information, and suggested therapy parameters to increase therapy efficacy.

In the example of FIG. 16A, screen 410 of user interface 408 presents orient information 436, operational menu 424, networking icon 414, printer icon 416, IMD communication icon 418, programmer battery icon 420, stimulation status icon 422, patient data icon 426, data recording icon 428, device status icon 430, programming icon 432, and data reporting icon 434. In addition, screen 410 includes posture state selections 438A, 438B, 438C, 438D, and 438E (collectively "posture state selections 438"), reset button 440, help button 442, and orient button 444. Screen 410 may be accessed by selecting programming icon 432 to open a drop down menu that allows the user to select one of multiple different screens. The user may select "orient device" or some other text or icon that symbolizes access to the process for initializing the orientation of sensor 40 within IMD 12.

Screen 410 includes multiple menus and icons common to other screens of user interface 408. Operational menu 424 is a button that the user may select to view multiple options or preferences selectable by the user. Operational menu 424 may provide preferences for programmer 20 instead of therapy specific information. Networking icon 414 may, in one embodiment, be grayed out to indicate that programmer 20 is not currently connected to a network. When networking icon 414 is shown fully, programmer 20 is connected to a network. Printer icon 416 indicates when programmer 20 is connected to a printer. When printer icon 416 is grayed out as shown in FIG. 16A, there is no printer connected to programmer 20.

Further, IMD communication icon 418 is shown as indicating that clinician programmer is not in communication with IMD 12 because the icon includes a slash through the IMD representation. The slash is removed when programmer 20 has established a communication link to IMD 12. In addition, programmer battery icon 420 indicates the current charge level of the battery contained within programmer 20. Stimulation status icon 422 indicates to the user when stimulation is being delivered to patient 14. Stimulation is not currently being delivered, but stimulation status icon 422 may include an electrical bolt through the IMD representation when stimulation is delivered.

Screen 410 also provides menu options related to stimulation therapy of patient 14. Patient data icon 426 allows the user to enter and review data related to the status of and the condition of patient 14. Data recording icon 428 allows the user to navigate to other screens to enter data recording preferences and review stored data. Device status icon 430 allows the user to view operational status of components of IMD 12, such as electrodes, leads, batteries, and any discovered problems. Programming icon 432 allows the user to navigate to programming screens that define the stimulation therapy parameters used to deliver stimulation to patient 14. In addition, data reporting icon 434 allows the user to view and print reports of patient 14 progress and other therapy information.

Specific to screen 410 of user interface 408, the clinician may initialize the orientation of the sensor 40 of IMD 12 by helping patient 14 assume each of posture states associated with selections 438 and setting the output of the sensor 40 to that particular posture state selection. Orient information 436, while not necessary in all examples, is provided to instruct the clinician on how to orient IMD 12 to patient 14. For example, FIG. 16A shows that the clinician has selected posture state selection 438A. Once patient 14 has assumed the standing position, the clinician would select orient button 444 to have IMD 12 set the sensor 40 output to the standing posture state. The clinician would repeat this process for each of posture state selections 438, in any order that the clinician chooses. In other examples, the clinician may not need to orient IMD 12 to each of the five posture state selections 438. IMD 12 may only require three posture state selections, such as Upright, Face Up, Face Down, and one of Left Side or Right Side.

The step of orienting IMD 12 may be necessary in an embodiment wherein defined vectors and detected vectors (e.g., defined posture vectors, detected posture vectors, defined activity vectors, detected activity vectors) are to be sensed, recorded and/or processed in the coordinate system of the sensor without regard to the patient's coordinate system. As discussed above, this ability to utilize vectors in the coordinate system of the sensor 40 provides processing efficiencies not afforded by systems that require transformation of vectors before posture state classification can occur.

In one embodiment, user interface 408 may prevent the clinician from using the IMD 12 for posture classification purposes unless the clinician has oriented IMD 12 to patient 14. In this manner, any further definition of posture states can only occur after orientation has been completed.

Figure 16B:
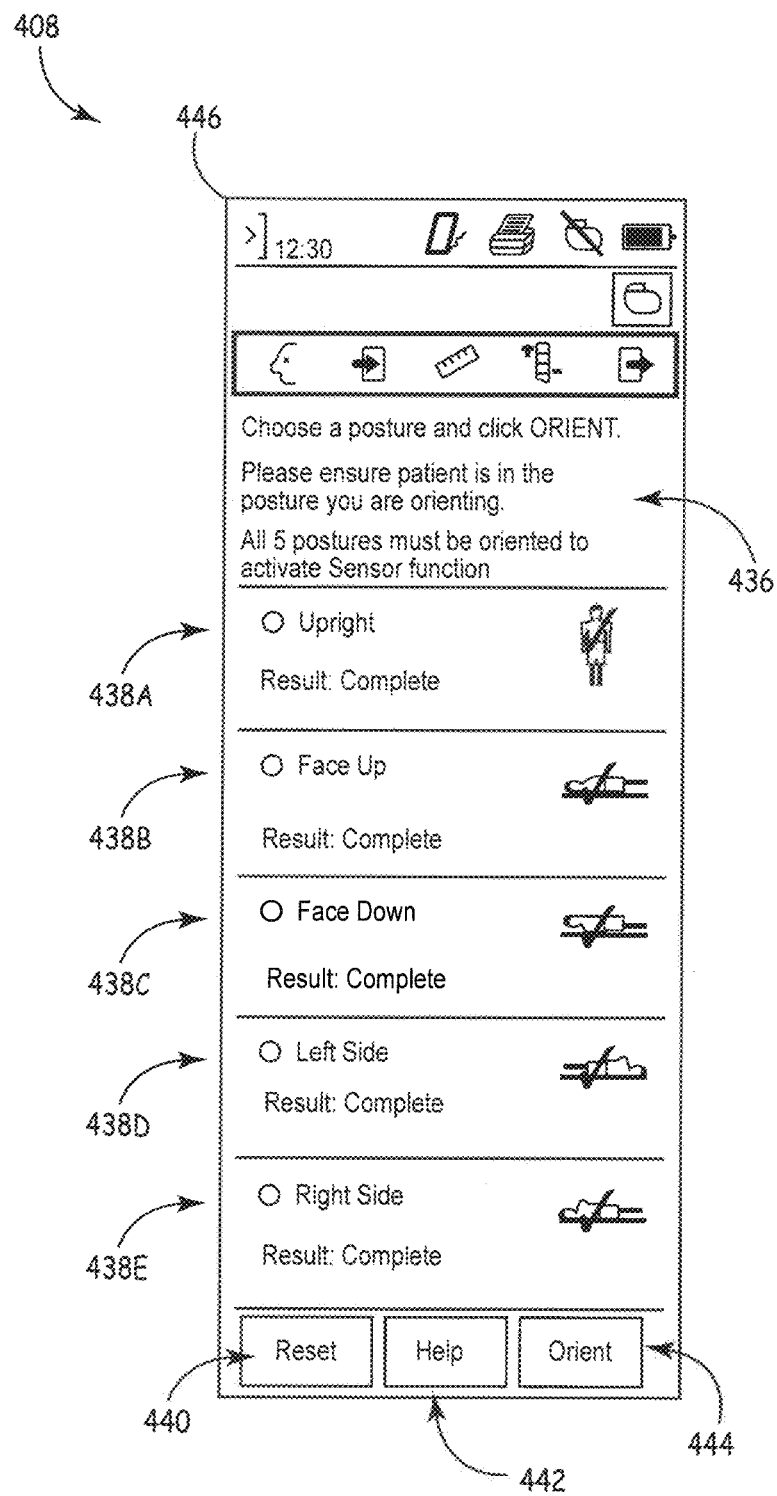

FIG. 16B is a conceptual diagram illustrating an example user interface 408 showing a user that orientation of the implantable medical device is complete. As shown in FIG. 16B, screen 446 of user interface 408 indicates to the clinician that orientation of IMD 12 has been completed for each of the posture state selections 438 as described in FIG. 16A. Each of the posture state selections 438 has a check mark through the graphical posture state indication on the right side of screen 446 to indicate that each posture state selection 438 has been oriented. Further, orient button 444 may be grayed out in one embodiment so that the clinician cannot select this function. Once programmer 20 is presented with screen 446, the clinician may continue defining posture states that utilize the defined vectors, if desired, or initiate other programming tasks that involve sensing of the posture state of patient 14. In alternative examples, programmer 20 may automatically enter a mode to allow posture state definition to continue once IMD 12 has been oriented to patient 14.

Figure 17A:
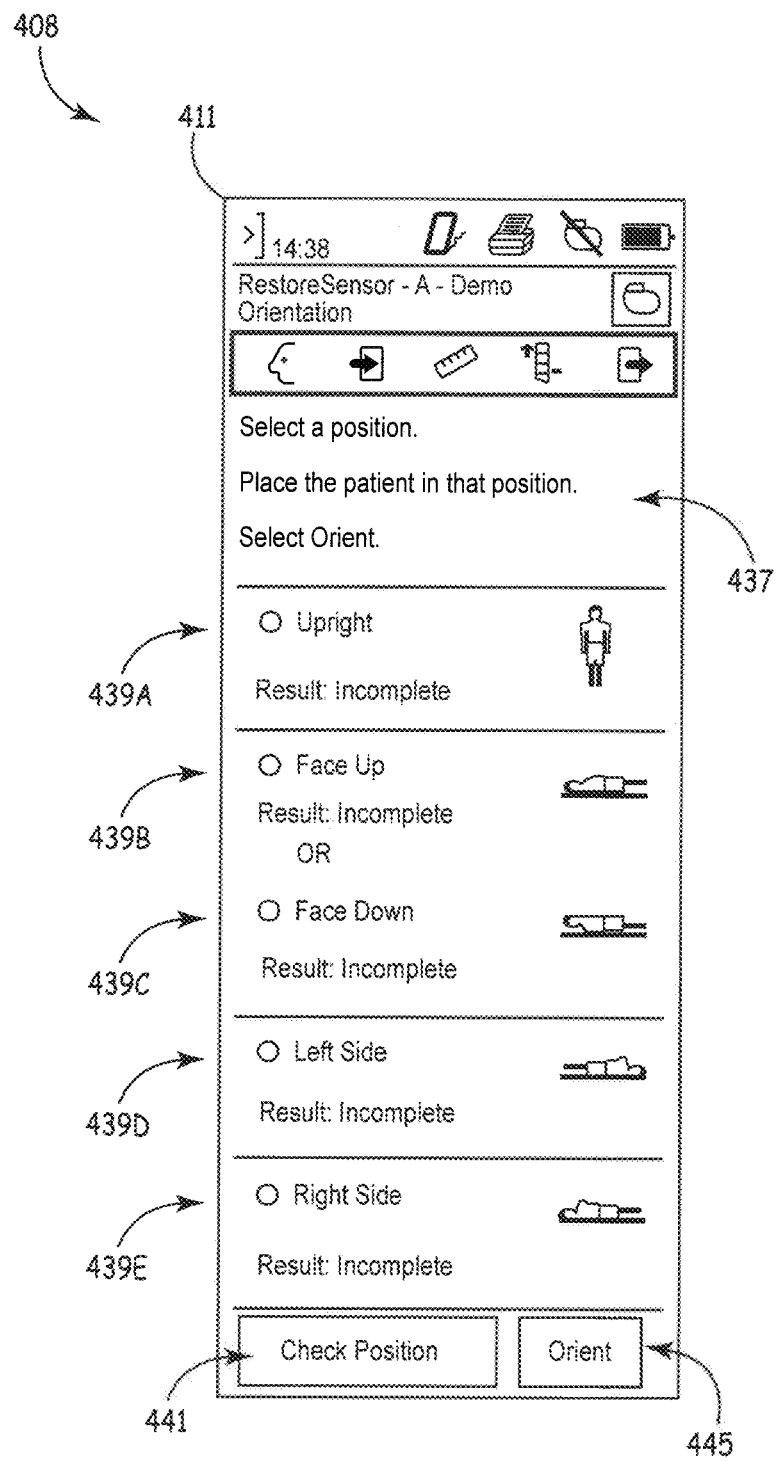
FIGS. 17A and 17B are conceptual diagrams illustrating an example user interface to determine orientation of an implantable medical device without requiring each posture state for orientation.
Figure 17B:
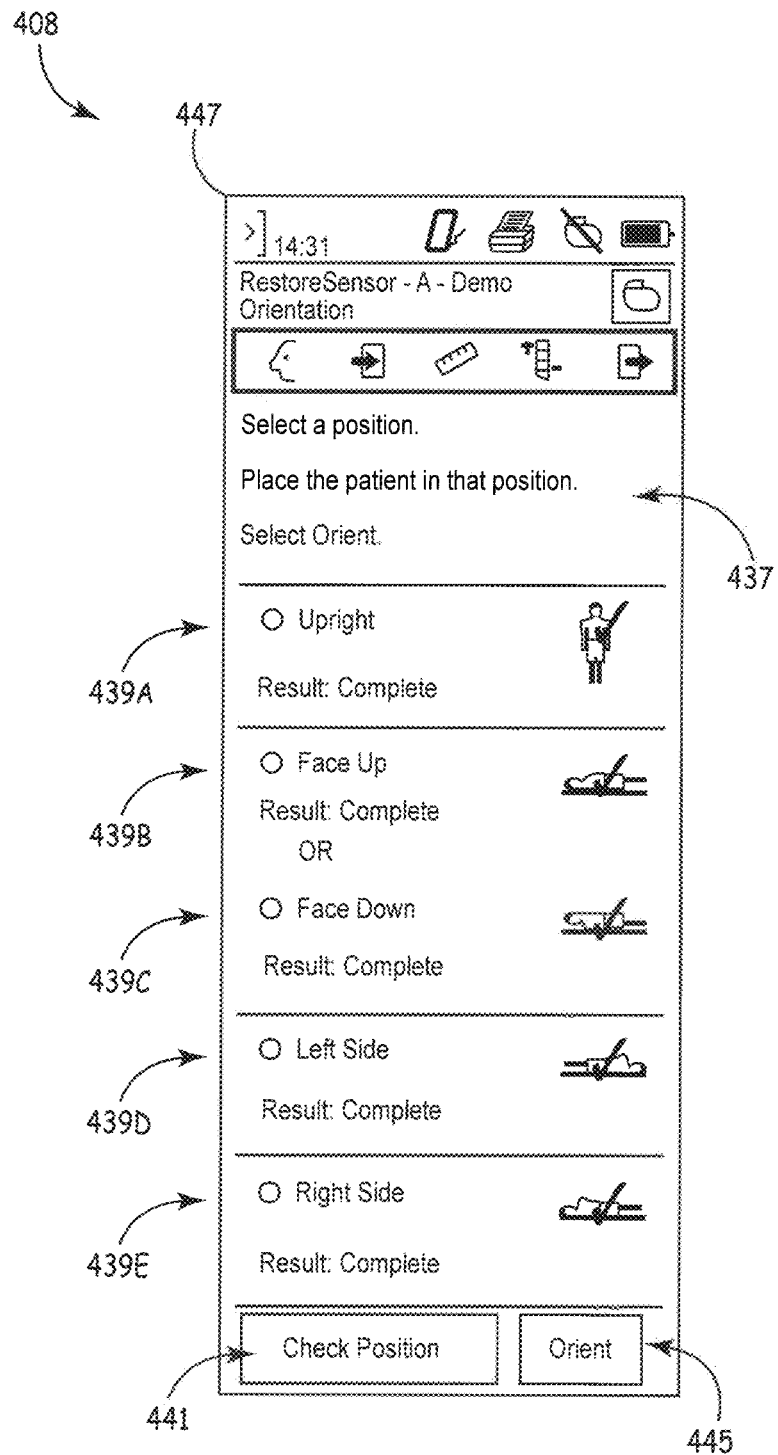

FIGS. 17A and 17B are conceptual diagrams illustrating an example user interface to determine orientation of an implantable medical device without requiring a patient to occupy each posture state for orientation. FIGS. 17A and 17B illustrate example screens 411 and 447 of user interface 408 that are substantially similar to screens 410 and 446 of FIGS. 16A and 16B. However, the example of FIGS. 17A and 17B only requires that patient 14 assumes four posture states of the possible five posture states in order to orient IMD 12 to patient 14, since the Face Down posture state is assumed to be an exact opposite of the Face Up posture state in this embodiment.

As shown in FIG. 17A, screen 411 of user interface 408 presents orient information 437, posture state selections 439A, 439B, 439C, 439D, and 439E (collectively "posture state selections 439"), position button 441, and orient button 445. The user may select "orient device" or some other text or icon that symbolizes access to the process for initializing the orientation of the sensor 40 within IMD 12.

Screen 411 allows the clinician to initialize the orientation of the sensor 40 of IMD 12 by helping patient 14 assume some of the possible posture states that IMD 12 may detect. Once patient 14 has assumed the appropriate types of posture states indicated by posture state selections 439, the sensor 40 of IMD 12 will be oriented, or calibrated, with pertinent defined posture vectors to function as described in this disclosure.

As discussed above, once the defined posture vectors are obtained via the user interface, these vectors may be used to define posture states, as by defining tolerances describing relationships to the vectors. Such tolerances may describe cones, toroids, or other regions in space relative to these vectors that can be used to define posture states. In some examples, a defined posture vector may be used to define an upright cone for an Upright posture, and to further define a cone or toroid that is used to detected a Lying Down posture.

Other vectors may be used to define other sub-classifications of the Lying Down posture (e.g., Right Side, Left Side, Face Up, Face Down, etc.)

In the example of FIG. 17A, although there are five possible posture states, screen 411 only requires that patient 14 assume four of the five posture states. In any particular order, the clinician orients IMD 12 to the Upright, Face Up, Face Down, Left Side, and Right Side posture states indicated by posture state selection 439A, 439B, 439C, 439D and 439E, respectively.

The clinician may orient each of these posture states by clicking on the appropriate posture state selection 439, ensuring that patient 14 has assumed that particular posture state, and selecting orient button 445. A sensed vector is then assigned to the posture state selection as a defined posture vector for use in posture detection according to any of the posture detection techniques described in this disclosure. At any time, the clinician may verify the posture state that IMD 12 is currently detecting patient 14 by selecting position button 441. Upon selecting position button 441, user interface 408 may provide an indication of the current posture state of patient 14. Once each of these posture states is oriented, therapy may proceed as described in this disclosure.

As shown in FIG. 17B, screen 447 of user interface 408 indicates to the clinician that orientation of IMD 12 has been completed for each of the posture state selections 439 as described in FIG. 17A. Each of the posture state selections 439 has a check mark through the graphical posture state indication on the right side of screen 447 to indicate that each posture state selection 439 has been oriented. It should be noted that in an embodiment wherein a Face Up posture state is an "opposite" of the Face Down posture state, once either the Face Up or Face Down posture state has been oriented, both posture state selections 439B and 439C will be checked as completed.

In particular, in an embodiment wherein the defined posture vectors for the Face Up and Face Down posture states are to be in exactly opposite directions from one another, once a defined posture vector is obtained for one of the Face Down or Face Up posture states, the inverse of that defined posture vector may be used for the other of the Face Down or Face Up posture states. For example, if the defined posture vector is obtained for the Face Down posture state, then the defined posture vector for the Face Up posture state is simply the inverse of the Face Down defined posture vector, and the actual defined posture vector for the Face Down posture state need not be obtained. In a similar manner, in an embodiment wherein the Right Side and Left Side defined posture vectors are to be exact opposites of one another, the patient need only assume one of the posture states, since both vectors can be determined using this one position.

The exemplary user interfaces of FIGS. 16A-17B provide only one example of the many types of posture states that may be defined using techniques discussed herein. The posture states may involve activity in addition to, or instead of, posture. In such cases, the patient will be required to begin the activity in order to orient the device. Thus, many other embodiments are possible, and this is only one illustration.

The example embodiments described herein utilize various efficiencies for performing detection and classification of postures and activity states. The efficiencies may include detecting a vector (e.g., a posture vector or activity state vector) in a coordinate system of a sensor without regard to a patient's coordinate system. This vector is then used to classify a patient's posture state without reference to the patient's coordinate system.

Such efficiencies may further include classification using non-angular similarities that do not require derivation of angles. Definitions for either postures or activity states may reference multiple regions in space, including one or more toroids and/or one or more cones. Such regions may be interrelated using Boolean Logic, if desired. In one embodiment, regions may be "overlaid" one upon another.

Other efficiencies relate to use of virtual vectors that are derived based on actual vectors obtained from a patient while a patient assumes a known posture or begins a known activity. Such virtual vectors, like the actual defined posture vectors, may be used to define postures and activity states.

Another aspect relates to evaluating a condition for use in selecting an aspect of a posture or activity state definition. For instance, the evaluation may select the size of the cone used by the posture or activity state definition.

Any of the one or more efficiencies and aspects described herein may be used for posture definition and classification, activity state definition and classification, or both. Moreover, any efficiency may be used alone, or combined with any other efficiency. Thus, many embodiments of a system are possible within the scope of the disclosure.

In the description above, the various functions, steps, techniques and mechanisms may be performed by processor 34 operating in conjunction with posture state module 41 and/or memory 36 of IMD 12. However, in other examples, data processing and storage may be distributed in a different manner between devices of a therapy system. For example, some of the processing steps to process signals from sensor 40 and classify the posture state of the patient may be performed by a processor of programmer 20 that receives signals from IMD 12 via telemetry communication, for instance. The programmer 20 may then initiate a response based on the posture state classification, and/or may issue a command to IMD 12 to cause the IMD to initiate some response, as will be necessary when the response involves starting, stopping, or modifying therapy being delivered to patient 14 by the IMD 12. In some cases, processor 34 of IMD 12 may perform some processing steps, transmit intermediate information to programmer 20, and the programmer will perform some steps, and re-transfer information to the IMD to complete processing. Many combinations of, and ordering of steps, are possible. In another example, at least some processing may be offloaded from IMD 12 or programmer 20 to a remote device including, e.g., a server that is wireless or otherwise coupled to programmer 20.

In any of the embodiments, posture state definitions 52 may be stored by IMD 12 and/or programmer 20. For instance, both programmer and IMD 12 may store a copy of this information.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to cause one or more processors to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Those skilled in the art will recognize that other modifications may be made to the systems, methods, and techniques described herein. For instance, some of the steps of the methods may be implemented in hardware such as posture state module 41. In many cases, steps may be re-ordered, and some steps may be eliminated. Thus, the description of the embodiments is merely exemplary, with the scope of the invention to be defined by the Claims that follow.

What is claimed is:

1. A method of classifying a posture state of a patient, comprising:
   obtaining a defined vector from at least one sensor disposed in a substantially fixed manner relative to the patient, the defined vector being described in a coordinate system of the at least one sensor and without regard to an orientation in which the sensor is disposed in relation to the patient;
   obtaining a detected vector from the at least one sensor, the detected vector being described in the coordinate system of the at least one sensor and being indicative of the posture state of the patient;
   comparing the detected vector and the defined vector;
   classifying the posture state of the patient based on the comparison and without regard to the orientation in which the sensor is disposed in relation to the patient; and
   initiating via a medical device an action related to providing care for the patient, the action being based on the posture state classification.

2. The method of claim 1, wherein obtaining the defined vector includes:
   measuring outputs of the at least one sensor while the patient assumes a defined posture state; and
   associating the measured outputs with the defined vector.

3. The method of claim 1, further comprising associating a region in space with the defined vector, and wherein comparing the detected vector and the defined vector further comprises determining whether the detected vector lies within the region in space.

4. The method of claim 3, further comprising:
   obtaining multiple defined vectors, each being associated with a respective region in space; and
   wherein comparing the detected vector and the defined vector comprises determining whether the detected vector lies within any of the regions in space associated with the multiple defined vectors.

5. The method of claim 1, further comprising:
   associating a tolerance with the defined vector; and
   determining a similarity between the defined vector and the detected vector; and
   wherein comparing the detected vector and the defined vector comprises comparing the similarity to the tolerance.

6. The method of claim 5, wherein the similarity is a distance, and further comprising:
   mapping the distance to a value that is directly proportional to a degree of similarity between the defined vector and the detected vector; and
   wherein comparing the detected vector and the defined vector comprises comparing the value to the tolerance.

7. The method of claim 1, further comprising:
   obtaining multiple defined vectors;
   associating each of the multiple defined vectors with a respective tolerance;
   interrelating multiple ones of the tolerances; and
   wherein comparing the detected vector and the defined vector comprises comparing the detected vector to a region in space described by the interrelated multiple ones of the tolerances.

8. The method of claim 7, wherein interrelating multiple ones of the tolerances comprises using one or more logical functions.

9. The method of claim 7, wherein the region in space is defined by a toroid and at least one cone.

10. The method of claim 1, further comprising:
    associating multiple tolerances with the defined vector, each indicating a relationship to the defined vector;
    evaluating a condition;
    selecting one of the multiple tolerances based on the evaluation; and
    wherein comparing the detected vector and the defined vector comprises determining whether the detected vector satisfies a relationship to the defined vector indicated by the selected one of the multiple tolerances.

11. The method of claim 10, further comprising:
    obtaining at least one other defined vector; and
    wherein evaluating the condition comprises comparing the detected vector to the at least one other defined vector.

12. The method of claim 11, further comprising:
    determining whether the detected vector is closer to a defined vector for a Face Up posture or a defined vector for a Face Down posture; and
    selecting a size of a region in space disposed about a defined vector for a Lying Down posture based on the determination; and
    wherein comparing the detected vector and the defined vector comprises comparing the detected vector to the region in space to determine whether the patient is in the Lying Down posture.

13. The method of claim 1, further comprising:
    deriving one or more constants based on at least one of a squared length of the defined vector and a size of a cone surrounding the defined vector;
    associating the one or more constants with the defined vector; and
    using the one or more constants to compare the detected vector and the defined vector.

14. The method of claim 13, further comprising normalizing the defined vector to have a selected length.

15. The method of claim 1, further comprising:
    obtaining multiple defined vectors;
    comparing the detected vector to ones of the multiple defined vectors; and
    if, based on the comparison, the patient is not classified as being in a posture state associated with any of the ones of the multiple defined vectors, generating refinement information to identify to which of the ones of the multiple defined vectors the detected vector is closest.

16. The method of claim 1, further comprising:
obtaining multiple defined vectors;
processing ones of the multiple defined vectors to obtain a virtual vector; and
comparing the detected vector and the virtual vector to classify the posture state of the patient.

17. The method of claim 16, wherein comparing the detected vector and the defined vector determines whether the patient is in an Upright posture, and further comprising comparing the detected vector to the virtual vector to determine whether the patient is in a Lying Down posture.

18. The method of claim 17, further comprising:
obtaining multiple additional defined vectors, each being associated with a posture that may be assumed when the patient is prone; and
if the patient is classified as being in the Lying Down posture, comparing the detected vector to one or more of the additional defined vectors to classify the patient as being in one of the postures that may be assumed when the patient is prone.

19. The method of claim 16, wherein comparing the detected vector to the virtual vector comprises determining whether the detected vector falls within any one of multiple regions of space disposed about the virtual vector.

20. The method of claim 16, wherein ones of the multiple defined vectors are each associated with a respective posture the patient may assume when the patient is prone;
obtaining a cross-product between multiple adjacent pairs of the ones of the multiple defined vectors; and
averaging the cross-products to obtain the virtual vector.

21. The method of claim 1, further comprising:
obtaining multiple defined vectors;
classifying the posture state of the patient based on a comparison between the detected vector and each of the multiple defined vectors; and
if the patient is not classified as being in a posture state associated with any of the multiple defined vectors, generating posture refinement information to identify to which of the multiple defined vectors the detected vector is closest.

22. The method of claim 1, further comprising:
obtaining multiple defined vectors;
deriving an inner product between the detected vector and multiple ones of the defined vectors; and
based on the derived inner products, classifying the patient as being in a posture state associated with the one of the multiple ones of the defined vectors to which the detected vector is closest.

23. The method of claim 1, wherein the defined vector and the detected vector are each associated with a direction of motion of the patient, and wherein classifying the posture state of the patient comprises classifying motion of the patient.

24. The method of claim 1, wherein the action comprises adjusting a manner in which therapy is being delivered to the patient.

25. An implantable medical device to determine a posture state of a patient, comprising:
a sensor configured to be substantially fixed to a patient without regard to sensor orientation and to provide signals indicative of a detected vector;
a storage device configured to store at least one posture state definition referencing at least one defined vector expressed in a coordinate system of the sensor; and
a processor configured to obtain the detected vector in the coordinate system of the sensor, to compare the detected vector to the at least one defined vector and to classify a posture state of the patient based on the comparison and without regard to sensor orientation.

26. The device of claim 25, wherein the at least one defined vector describes motion of the patient, and the processor is configured to classify the posture state of the patient based on the motion.

27. The device of claim 25, further comprising a therapy module configured to provide therapy to the patient based on the classification of the posture state.

28. The device of claim 27, wherein the therapy module delivers electrical stimulation therapy to the patient based on the classification of the posture state.

29. The device of claim 25, wherein the at least one posture state definition references a tolerance describing a relationship to the defined vector, and the processor is configured to classify the posture state based on whether the detected vector has the relationship to the at least one defined vector.

30. The device of claim 25, wherein the processor is configured to classify the posture state based on a similarity between the detected vector and each of the at least one defined vector, the similarity being derived without derivation of an angle.

31. The device of claim 25, wherein the processor is configured to classify the posture state based on a determination as to which of the at least one defined vector the detected vector is closest.

32. The device of claim 25, wherein the at least one posture state definition takes into account at least one of posture and activity state of the patient.

33. The device of claim 25, wherein the at least one posture state definition references multiple defined vectors, and the processor is configured to process ones of the multiple defined vectors to obtain a virtual vector, and to classify the posture state of the patient based on a comparison between the detected vector and the virtual vector.

34. The device of claim 33, wherein the processor is configured to obtain multiple adjacent pairs of the ones of the multiple defined vectors, to obtain a cross-product for each of the multiple adjacent pairs, and to average the cross-products to obtain the virtual vector.

35. The device of claim 34, wherein the processor is configured to compare the detected vector to a defined vector for an Upright posture to determine whether the posture state involves an Upright posture, and if not, to compare the detected vector to the virtual vector to determine whether the posture state involves a Lying Down posture.

36. The device of claim 25, wherein the at least one posture state definition references multiple defined vectors, each being associated with a respective tolerance, and wherein a function describes a relationship between the tolerances, and the processor is configured to determine whether the detected vector lies within a region of space described by the relationship between the tolerances.

37. The device of claim 36, wherein at least one of the tolerances describes a toroid surrounding a defined vector for an Upright posture, a different one of the tolerances describes a cone surrounding a defined vector for a posture assumed when a patient is in a prone position, and the relationship is a logical OR function.

38. A method, comprising:
receiving a defined vector from at least one sensor carried in any orientation within a patient, the defined vector being expressed in a coordinate system of the at least one sensor and without regard to the coordinate system of the patient;

defining a posture state in reference to the defined vector;

obtaining a detected vector from the at least one sensor communicatively coupled to an implantable medical device, the detected vector being expressed in the coordinate system of the at least one sensor and without regard to the coordinate system of the patient;

classifying the posture state of the patient based on a comparison between the detected vector and the defined vector; and delivering therapy to the patient via the implantable medical device based on the posture state classification.

39. The method of claim 38, wherein defining the posture state comprises defining an activity state describing motion of the patient, and wherein the determining step determines whether the patient is engaged in the motion.

40. The method of claim 38, wherein the defined vector is one of a velocity vector and an acceleration vector.

41. The method of claim 38, further comprising:
receiving multiple defined vectors from the at least one sensor;
selecting a respective tolerance for each of the multiple defined vectors;
defining the posture state in reference to ones of the multiple defined vectors and the respective tolerances; and
wherein classifying the posture state of the patient comprises determining whether the detected vector falls within a region in space defined by the posture state definition.

42. The method of claim 38, further comprising:
associating the posture state definition with multiple tolerances and a condition; and
wherein classifying the posture state of the patient comprises evaluating the condition to select one of the multiple tolerances and performing the comparison based on the selected one of the multiple tolerances.

43. The method of claim 39, wherein classifying the posture state of the patient comprises deriving a similarity between the detected vector and the defined vector for use in the comparison between the detected vector and the defined vector.

44. The method of claim 43, wherein the similarity is a distance, and further comprising mapping the distance to a value between 0 and a selected maximum similarity value.

45. A non-transitory storage medium storing executable instructions to cause a processor to perform the method, comprising:
obtaining a detected vector from signals of a sensor, wherein the sensor is carried in any fixed orientation relative to a patient, and wherein the detected vector is indicated in a coordinate system of the sensor;
obtaining one or more posture state definitions that reference one or more defined vectors, each defined vector being indicated in the coordinate system of the sensor;
comparing the detected vector directly to the one or more defined vectors; and
based on the comparison, classifying a posture state of the patient.

46. A system, comprising:
a sensor disposed in any substantially fixed position relative to a patient and configured to provide signals indicative of a detected vector; and
one or more processors configured to obtain a defined vector expressed in a coordinate system of a sensor wherein the defined vector is associated with a posture state definition, to obtain the detected vector in the coordinate system of the sensor, to compare the detected vector to the defined vector, and to classify a posture state of the patient based on the comparison and without regard to the orientation in which the sensor is disposed in relation to the patient.

47. The system of claim 46, further comprising a device external to the patient that comprises one of the one or more processors.

48. The system of claim 47, wherein the device external to the patient is a programmer.

49. The system of claim 48, wherein the programmer includes a user interface to provide information about the posture state of the patient.

50. The system of claim 47, further comprising an implantable medical device comprising one of the one or more processors, and wherein the implantable medical device is configured to communicate with the device external to the patient.

51. The system of claim 46, further comprising an implantable medical device comprising one of the one or more processors.

52. The system of claim 51, wherein the implantable medical device is configured to deliver therapy to the patient based on the classification of the posture state of the patient.

53. The system of claim 46, wherein the at least one defined vector describes motion of the patient, and the processor is configured to classify the posture state of the patient based, at least in part, on the motion.

54. The system of claim 46, wherein the defined vector is associated with a tolerance that describes a relationship to the defined vector, and the processor is configured to classify the posture state based on whether the detected vector has the relationship to the at least one defined vector.

55. The system of claim 46, wherein the processor is configured to classify the posture state based on a similarity between the detected vector and each of the at least one defined vector, the similarity being derived without derivation of an angle.

* * * * *